(12) United States Patent
Yoo et al.

(10) Patent No.: US 10,327,691 B2
(45) Date of Patent: Jun. 25, 2019

(54) SYSTEMS AND METHOD FOR DETECTING, DIAGNOSING, AND/OR TREATMENT OF DISORDERS AND CONDITIONS

(71) Applicant: Khalifa University of Science and Technology, Abu Dhabi (AE)

(72) Inventors: Jerald Yoo, Abu Dhabi (AE); Muhammad Altaf, Abu Dhabi (AE); Chen Zhang, Abu Dhabi (AE)

(73) Assignee: Khalifa University of Science and Technology (AE)

( * ) Notice: Subject to any disclaimer, the term of this patent is extended or adjusted under 35 U.S.C. 154(b) by 341 days.

(21) Appl. No.: 15/048,370

(22) Filed: Feb. 19, 2016

(65) Prior Publication Data

US 2016/0249846 A1    Sep. 1, 2016

Related U.S. Application Data

(60) Provisional application No. 62/117,971, filed on Feb. 19, 2015.

(51) Int. Cl.
*A61B 5/00* (2006.01)
*A61B 5/04* (2006.01)
(Continued)

(52) U.S. Cl.
CPC .......... *A61B 5/4094* (2013.01); *A61B 5/0478* (2013.01); *A61B 5/0531* (2013.01);
(Continued)

(58) Field of Classification Search
None
See application file for complete search history.

(56) References Cited

U.S. PATENT DOCUMENTS

2014/0235990 A1  8/2014  Yoo et al.
2015/0038870 A1  2/2015  Yoo et al.

FOREIGN PATENT DOCUMENTS

WO  2013123358 A1  8/2013

OTHER PUBLICATIONS

Yoo et al. An 8-Channel Scalable EEG ACquisition SoC with Fully Integrated Patient-Specific Seizure Classification and Recording Processor. ISSCC 2012, Session 17, Diagnostic and Therapeutic Technologies for Health, 17.1.*

(Continued)

*Primary Examiner* — Etsub D Berhanu
(74) *Attorney, Agent, or Firm* — Hayes Soloway PC

(57) ABSTRACT

A SoC includes an AFE to receive a plurality of differential input channels and generate digitized data corresponding to the channels, and a classification processor configured to receive the digitized data from the AFE. The AFE includes a Dual-Channel Chopper to perform channel multiplexing of two channels while simultaneously chopping the channels, a Dual Channel Charge Recycled-AFE having an Chopper-Stabilized Capacitive-Coupled IA including bias sampling capacitors that store bias values associated with the first and second channels to enable swapping between the channel, and a DC servo loop (DSL) having a reduced setting time based on a reduction in a resistance of the pseudo-PMOS in response to engaging a system reset. The classification processor includes a Frequency-Time Division Multiplexing (FTDM) Feature Extraction (FE) engine and a Dual-Detector Architecture ($D^2A$) classification processor. The FTDM-FE includes a plurality of FIFOs configured to store, in parallel, the digitized data corresponding to the channels, a plurality of BPF banks storing BPF coefficients, and a single BPF to calculate outputs of one specific bank of the BFP banks for all of the channels. The $D^2A$ processor receives the (Continued)

output from the FTDM-FE and estimates a beginning and end of a seizure using two LSVMs optimized for only sensitivity and specificity, respectively.

16 Claims, 29 Drawing Sheets

(51) Int. Cl.
    *A61N 1/36*     (2006.01)
    *A61B 5/053*     (2006.01)
    *A61B 5/0478*     (2006.01)
    *G16H 50/20*     (2018.01)
    *G06F 19/00*     (2018.01)

(52) U.S. Cl.
    CPC ......... *A61N 1/36025* (2013.01); *G06F 19/00* (2013.01); *G16H 50/20* (2018.01); *A61B 5/6814* (2013.01); *A61B 2560/0209* (2013.01); *A61B 2562/164* (2013.01); *A61N 1/36064* (2013.01)

(56) References Cited

OTHER PUBLICATIONS

PCT International Search Report and Written Opinion dated Jul. 13, 2016, received in PCT Application No. PCT/IB16/00222, 17 pgs.
Alotaiby, T.N. et al: "EEG Seizure Detection and Prediction Algorithms: A Survey", EURASIP Journal on Advances in Signal Processing 2014, 2014:183, Dec. 23, 2014, pp. 1-21.
Altaf, M.A.B. et al: "A 1.83uJ/Classification Nonlinear Support-Vector-Machine-Based Patient-Specific Seizure Classification SoC", 2013 IEEE International Solid-State Circuits Conference Digest of Technical Papers, IEEE, Feb. 18, 2013, pp. 100-101.
Altaf, M.A.B. et al: "A 1.52uJ/Classification Patient-Specific Seizure Classification Processor using Linear SVM", 2013 IEEE International Symposium on Circuits and Systems (ISCAS2013), IEEE, May 19, 2013, pp. 849-852.
Chen, W.M. et al:"A Fully Integrated 8-Channel Closed-Loop Neural-Prosthetic CMOS SoC for Real-Time Epileptic Seizure Control", IEEE Journal of Solid-State Circuits, vol. 49, No. 1, Jan. 2014, pp. 232-247.
Jahankhani, P. et al: "EEG Signal Classification Using Wavelet Feature Extraction and Neural Networks", Proceedings of the IEEE John Vincent Atanasoff 2006 International Symposium on Modern Computing (JVA'06), IEEE Computer Society, Washington DC, USA, 2006, pp. 120-124.
Verma, N. et al: "A Micro-Power EEG Acquisition SoC With Integrated Feature Extraction Processor for a Chronic Seizure Detection System", IEEE Journal of Solid-State Circuits, vol. 45, No. 4, Apr. 2010, pp. 804-816.
Altaf, M.A.B. et al: "A 2.45uW Patient-Specific Non-Invasive Transcranial Electrical Stimulator With an Adaptive Skin-Electrode Impedance Monitor", IEEE Biomedical Circuits and Systems Conference (BioCAS), 2015 IEEE, Oct. 2015, 8 pgs.
Altaf, M.A.B. et al: "A 16 channel Patient-Specific Seizure Onset and Termination Detection SoC With Impedance-Adaptive Transcranial Electrical Stimulator", IEEE Journal of Solid-State Circuits, vol. 50, No. 11, Nov. 2015, pp. 2728-2740.
Alfat, M.A.B. et al: "A 16-ch Patient-Specific Seizure Onset and Termination Detection SoC with Machine-Learning and Voltage Mode Transcranial Stimulation", 2015 IEEE International Solid-State Circuits Conference, 41 pgs.
International Preliminary Report on Patentability dated Aug. 31, 2017, issued in PCT Patent Application No. PCT/IB2016/000222, 11 pages.

* cited by examiner

ARCHITECTURE

WAVEFORMS

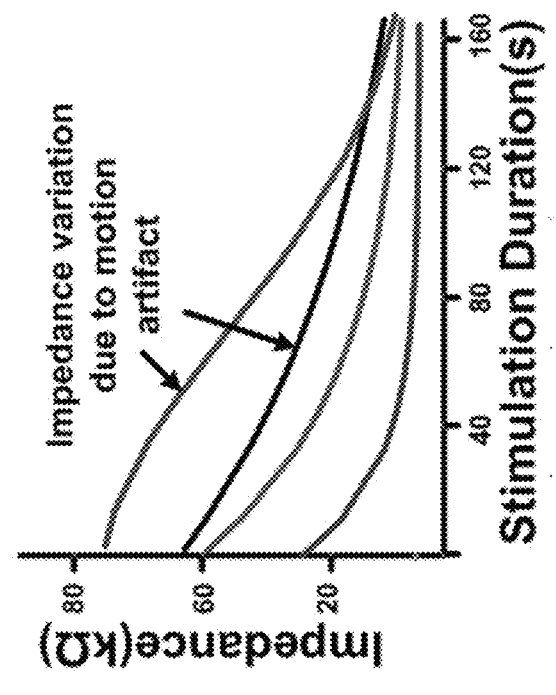
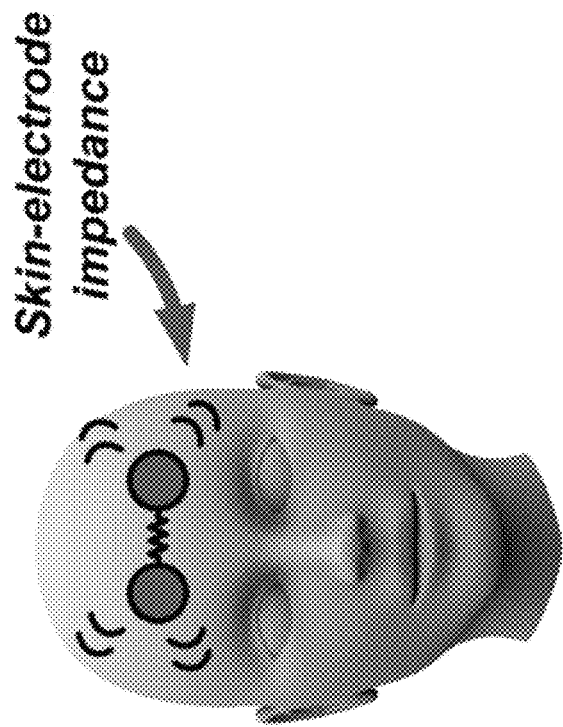
FIG. 14

TABLE I

| | N. Verma JSSC'10 [7] | J. Yoo JSSC'13 [10] | Y. Tsai ISSCC'15 [33] | Q. Fan JSSC'11 [35] | R. Yazicioglu JSSC'08 [36] | J. Xu JSSC'15 [37] | R. Muller JSSC'15 [38] | DDCR-AFE 16 |
|---|---|---|---|---|---|---|---|---|
| Supply (V$_{DD}$) | 1.0V | 1.8V | 1.8V | 1.0V | 3.0V | 1.8V | 0.5V | 1.8V |
| Current | 3.5µA | 1.4µA | 13.5µA/ch | 2.1µA | 2.3µA | 7.4µA | 4.6µA | 0.9µA/ch |
| Gain | 40dB | 40dB | 40dB | 40dB | 46dB | 36.9dB | 30dB | 40dB |
| Input Impedance | >700MΩ | >500MΩ | - | 80MΩ | 1GΩ | 1GΩ@1Hz | 28MΩ | >500MΩ |
| CMRR | 60dB | >100dB | 110dB | 134dB | 120dB | 102dB | 88dB | 97dB |
| Noise RTI | 1.3µV$_{rms}$ (100Hz) | 0.91µV$_{rms}$ (0.5-100 Hz) | 0.25µV$_{rms}$ (10-100 Hz) | 6.7µV$_{rms}$ (0.5-100 Hz) | 0.59µV$_{rms}$ (0.5-100 Hz) | 0.65µV$_{rms}$ (0.5-100 Hz) | 0.58µV$_{rms}$ (1-100 Hz) | 0.90µV$_{rms}$ (0.5-100 Hz) |
| On-Chip DSL | X | O | X | O | O | O | O | O |
| NEF | 11.0 | 5.1 | 3.74 | 3.3 | 4.1 | - | 4.76 | 3.29/ch |
| Max. EDO Rejection | Rail-To-rail | 200mV | X | 10mV | 45mV | 350mV | 50mV | 240mV |
| Technology | 0.18µm | 0.18µm 1P6M | 0.35µm | 0.18µm | 0.50µm | 0.18µm | 65nm | 0.18µm 1P6M |
| Application | Wearable EEG | Wearable EEG | ECG/EEG | Sensor Node | Ambulatory EEG | Wearable EEG | Implantable EEG | Wearable EEG |

FIG. 21

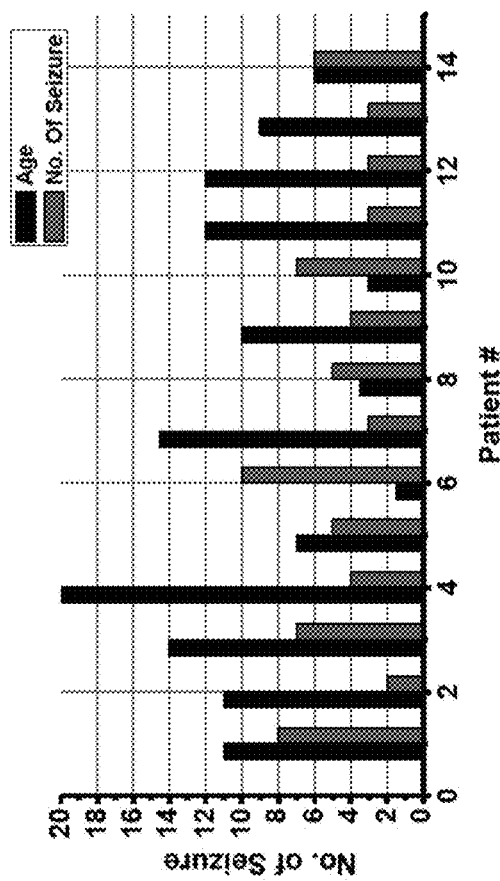
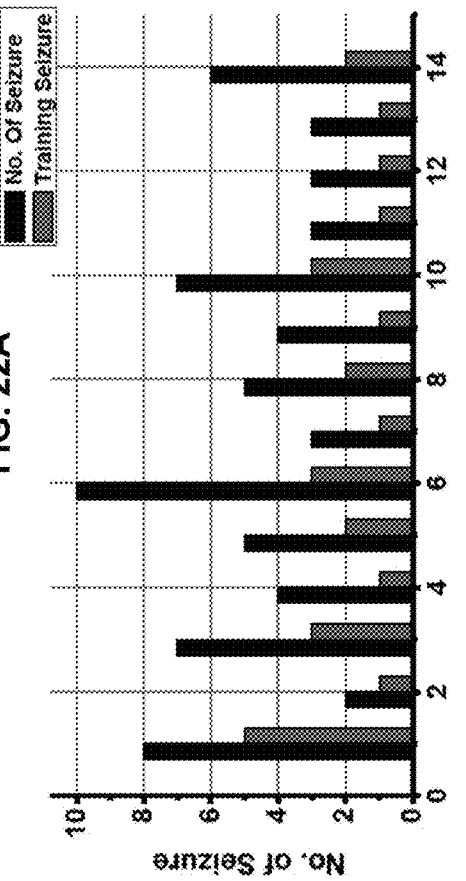
FIG. 22A
FIG. 22B

TABLE II

| | J. Yoo JSSC'13 [10] | M. Altaf TBioCAS'15 [12] | M. Mirzaei TBioCAS'13 [13] | W. Chen JSSC'14 [14] | K. Lee JSSC'13 [42] | D²A-LSVM 18 |
|---|---|---|---|---|---|---|
| Patient Specific | O | O | O | X | O | O |
| Seizure Termi. Detection | X | X | X | X | X | O |
| Sensitivity | 84.4% | >96% | 100% | 92% | 100% (by event) | 95.7% |
| Specificity | 96% | >99% | 100% | --- | 0.75 FA/H | 98.0% (0.27 FA/H) |
| Classifier | Linear SVM | Gaussian SVM | HFD | LLS | SVM | D²A-LSVM |
| System Latency | 2s | 2s | --- | 0.8s | --- | 1s |
| No. of Channels | 8 | 8 | 1 | 8 | 1 | 16 |
| On Chip Storage | O | O | X | X | X | O |
| Energy Efficiency | 1.49μJ/Class | 1.31μJ/Class | 44.85nW | 77.9μJ/Class | 273μJ/Class | 1.85μJ/Class |
| Technology | 0.18μm | 0.18μm | 0.18μm | 0.18μm | 0.13μm | 0.18μm |

FIG. 25

SYSTEMS AND METHOD FOR DETECTING, DIAGNOSING, AND/OR TREATMENT OF DISORDERS AND CONDITIONS

PRIORITY

The present non-provisional U.S. patent application claims benefit under 35 U.S.C. § 120 of U.S. Provisional Patent Application No. 62/117,971 entitled, "EPILEPSY DETECTION SYSTEM" that was originally filed on Feb. 19, 2015. The contents of the above-identified provisional application are incorporated herein, in entirety, by reference.

FIELD

The present disclosure is generally directed to systems and methods for electrophysiological monitoring, and more particularly, to systems and method for detecting neurological disorders and systems and methods for diagnosing and/or treating neurological disorders such as, but not limited to, epilepsy.

BACKGROUND

Epilepsy is a severe and chronic neurological disorder that affects more than 65 million people worldwide. It is characterized by recurrent seizures that occur after an episode of abnormal electrical activity in the brain, causing temporary loss of consciousness, convulsions, or confusion. As a disorder of the brain, it causes devastating abnormal synchronous discharges in the neural areas of the brain. Because of the huge variation in seizure patterns in subjects, patient-specific detection is difficult to diagnose but very crucial for intervention and treatment.

Antiepileptic drugs are the standard treatment for controlling and reducing epileptic seizures, but around 30% of patients cannot be effectively treated with medication. Deep Brain Stimulation (DBS) and Vagus Nerve Stimulation (VNS) therapy is a surgical treatment for people whose seizures are not controlled effectively by medication. DBS and VNS involves sending regular, mild pulses of electrical energy to the brain by implanting electrodes into specific areas of the brain and via the vagus, respectively. The VNS is placed under the skin on the chest wall, and a wire runs from it to the vagus nerve in the neck whereas surgery is needed to implant the DBS in the affected brain area. However, the surgery may lead to internal bleeding, infection, depression, incision scarring and is not effective in newborn/children/ICU-admitted patient group. Moreover, the implantable devices need to be replaced often to avoid infection, making the lifetime of the devices bound not by the battery life, but rather by pernicious caused in the body.

Up to now, there is no patient-friendly solution for seizure detection and stimulation that targets this alarmingly large population. While multichannel electroencephalography (EEG) seizure detection system on chips (SoCs) have been used in medical practice and in research, the existing multichannel EEG SoCs suffer from several limitations.

One limitation of existing multichannel EEG SoCs is that they have a limited number of channels. For example, existing multichannel EEG SoCs present less than or equal to 8 channel SoCs, whereas the American Clinical Neurophysiology Association sets the minimum technical standard recommendation for pediatric EEG of 16 channels with bipolar and referential montages.

Another limitation of existing multichannel EEG SoCs is that they while they may have good accuracy for seizure onset detection with patient specific approach, they lack seizure termination detection. As may be appreciated, seizure termination detection is crucial for medication and stimulation dose control.

Yet another limitation of existing multichannel EEG SoCs is that they involve invasive stimulation. For example, while some existing multichannel EEG SoCs implement an 8-channel closed-loop seizure detection SoC, these existing multichannel EEG SoCs are not patient-specific, and moreover, are invasive.

Experimental studies show that transcranial electrical stimulation (tES) is safe and efficient in reducing seizure frequency in drug-resistant epilepsy. Some systems have shown that a closed-loop tES may dramatically suppress spike-and-wave episodes in a rodent model of generalized epilepsy. While neuro-feedback system using tES for mental health treatment may exist, they lack patient-specificity and have a limited number of channels.

Turning now to FIG. 1, a variation in EEG pattern (as well as the delay between electrical onset and clinical onset) from three different epileptic patients is generally illustrated. Studies have shown that an electrical onset typically prevails a clinical onset by 0.5-10 s. The systems and methods of the present disclosure may include a non-invasive seizure mitigation system that features a SoCs that have both robust real-time, patient-specific seizure onset and termination detection and power-efficient non-invasive tES. Additionally, the systems and methods of the present disclosure also features the first fully integrated 16-channels SoC for seizure onset/termination detection with tES for seizure suppression, which can be potentially integrated in a wearable patch form-factor, thereby overcoming the above mentioned limitations of the available SoCs.

BRIEF DESCRIPTION OF THE DRAWINGS

FIG. 14 generally illustrates a skin-electrode impedance variation due to motion artifact, patient-to-patient and stimulation duration consistent with at least one embodiment of the present disclosure;

FIG. 21 is a comparison of channel shared DCCER-AFE consistent with at least one embodiment of the present disclosure with other systems;

FIG. 22A generally illustrates patient age and seizure occurrence wise distribution consistent with at least one embodiment of the present disclosure;

FIG. 22B generally illustrates training sample used per patient consistent with at least one embodiment of the present disclosure;

FIG. 25 is a comparison of $D^2A$ classification processor consistent with at least one embodiment of the present disclosure with other systems;

Figure 1:
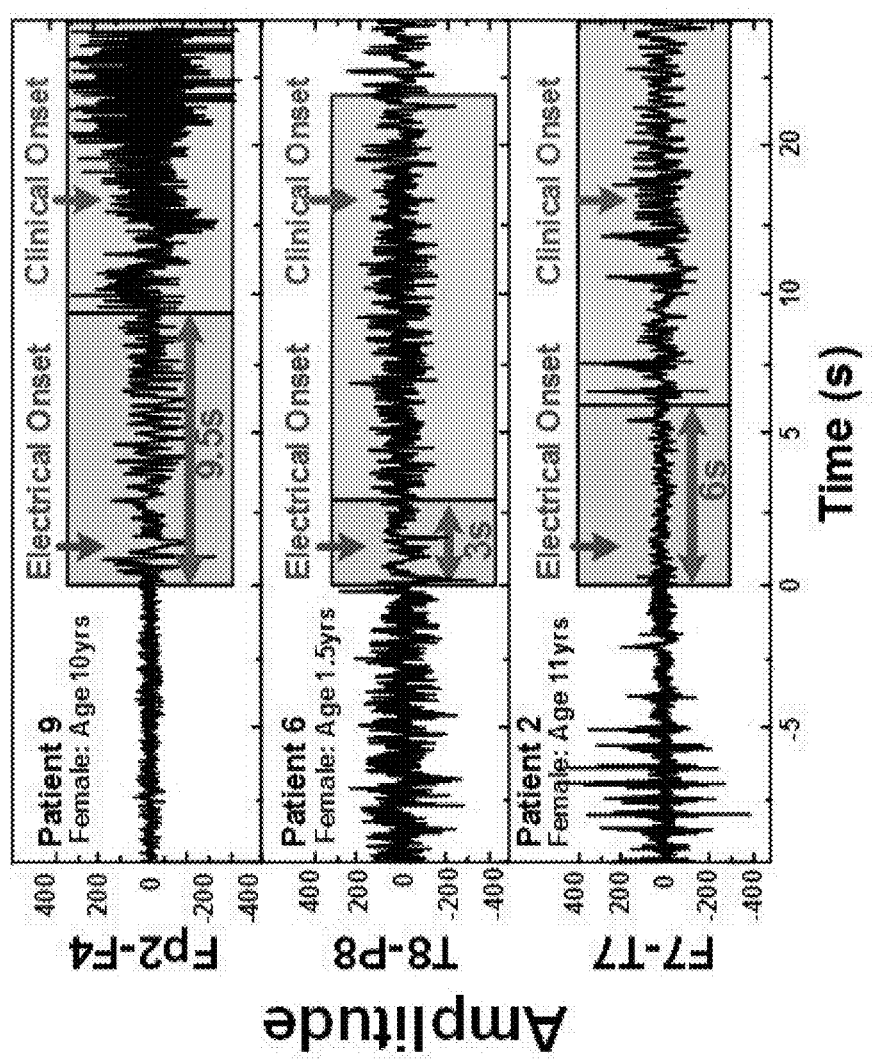
FIG. 1 generally illustrates variation in EEG pattern (as well as the delay between electrical onset and clinical onset) from three different epileptic patients.

These and other features of the present embodiments will be understood better by reading the following detailed description, taken together with the figures herein described. The accompanying drawings are not intended to be drawn to scale. In the drawings, each identical or nearly identical component that is illustrated in various figures is represented by a like numeral. For purposes of clarity, not every component may be labeled in every drawing.

DETAILED DESCRIPTION

In general, the present disclosure features systems and methods for electrophysiological monitoring (such as for detecting neurological disorders) as well as systems and methods for diagnosing and/or treating neurological disorders such as, but not limited to, epilepsy. According to one embodiment, the systems and method features a multichannel (e.g., but not limited to, 16-channel) patient-specific scalable electroencephalography (EEG) acquisition system on chip (SoC). The EEG acquisition SoC may continuously monitor and/or detect seizure onset and termination, and may also feature non-invasive impedance adaptive stimulation. The SoC may feature a multichannel (e.g., 16 channel) analog front-end (AFE) with a low-noise, low-power instrumentation amplifier (IA), a Dual-Detector Architecture ($D^2A$) classification processor, a patient-specific Pulsating Voltage Transcranial Electrical Stimulator (PVTES) and an memory (e.g., but not limited to, SRAM). The AFE may feature a Dual Channel Charge Recycled-AFE (DCCR-AFE) having an area and energy-efficient DCCR Chopper-Stabilized Capacitive-Coupled IA (CS-CCIA) to effectively incorporate two channels per IA and a fast-settling dc servo loop (FS-DSL) that achieves a settling time of 0.5 s or less. The DCCR-AFE may consume approximately 0.9 µA/channel with a NEF of 3.29/channel. A $D^2A$-Linear Support-Vector Machine ($D^2A$-LSVM) machine-learning classifier may exploit two area-efficient LSVM detectors with a digital hysteresis to achieve high sensitivity and specificity at once with a low latency of 1s. The SoC, which may be implemented in 0.18 µm 1P6M standard CMOS process with an area of 25 mm$^2$, may be verified with the CHB-MIT database as well as with specific-rapid eye blink tests, which shows the sensitivity and specificity of 95.7% and 98%, respectively, while consuming 2.73 µJ/classification.

Figure 2:
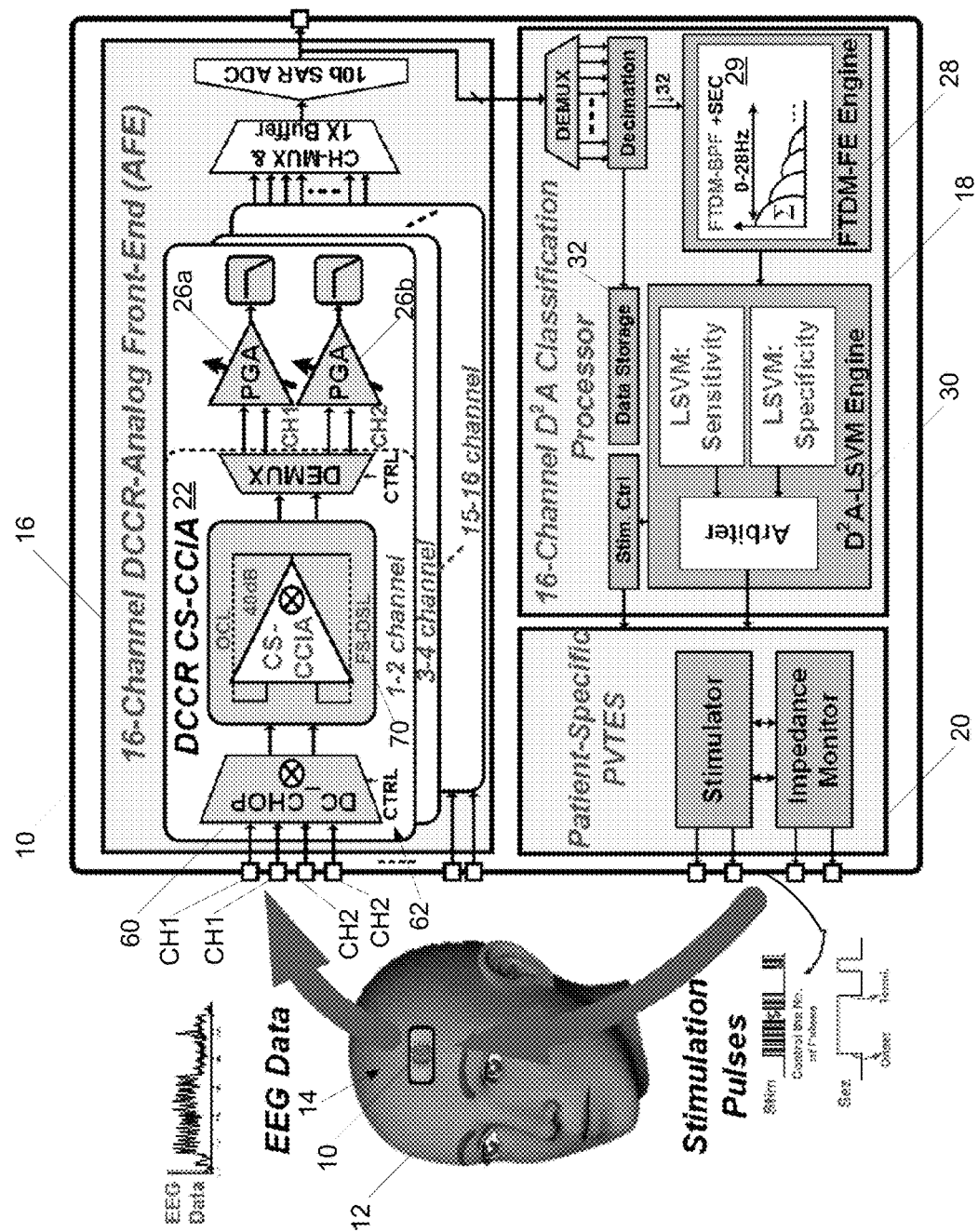
FIG. 2 generally illustrates a patient-specific scalable electroencephalography (EEG) acquisition system on chip (SoC) consistent with at least one embodiment of the present disclosure.

Turning now to FIG. 2, one embodiment generally illustrating the patient-specific scalable electroencephalography (EEG) acquisition system on chip (SoC) 10 is generally illustrated. As can be seen, the SoC may be placed and removably secured on a patient 12 such as, but not limited to, a portion of the external surface of the user's scalp 14 (though it is also possible to implant the SoC 10 underneath the user's skin). As described herein, the SoC 10 may detect electrical activity of the brain (e.g., neurological signals) which may be used to diagnosis and/or treat medical conditions such as, but not limited to, epilepsy, sleep disorders, comas, encephalopathies, brain deaths, tumors, strokes and other focal brain disorders.

By way of an overview, the SoC 10 may include multichannel (e.g., 16-channel) area- and-energy-efficient analog front-end (AFE) 16, classification processor 18, and optionally a patient specific treatment circuitry 20. For the sake of brevity, the following description will be described in the context of a SoC that includes 16 channels for the treatment of epilepsy, though it should be appreciated that the SoC could have greater than or fewer than 16 channels and may be used for the diagnosis and/or treatment of other medical conditions. Modifications to increase or decrease the number of channels are considered to be within the ordinary skill of the art based on instant disclosure.

The AFE 16 may include a 16-channel Dual Channel Charge Recycled-AFE (DCCR-AFE). The 16-channel DCCR-AFE 16 may include eight DCCR Chopper-Stabilized Capacitive-Coupled IA (CS-CCIA) 22 operating in continuous time domain, where each of the two channels (e.g., CH1, CH2) are followed by a discrete time-domain Programmable Gain Amplifier (PGA) 26a, 26b. The digitized data is then processed by the classification processor 18 (e.g., a Dual-Detector Architecture ($D^2A$) classification processor). The classification processor 18 may include a Frequency-Time Division Multiplexing (FTDM) Feature Extraction (FE) engine 28 followed by a $D^2A$-Linear Support Vector Machine (LSVM) engine 30. The dual LSVM classifier 18 enhances both sensitivity and specificity at once by implementing a digital hysteresis. Once the seizure is detected, the patient specific treatment circuitry 20 (which may include a low-power Pulsating Voltage Transcranial Electrical Stimulator (PVTES)) automatically adapts the number of pulses with respect to skin-electrode impedance variation to ensure constant charge delivery. At the same time, the processor records the raw EEG data before and after the clinical onset into memory (e.g., on-chip 64 KB-SRAM 32) for further analysis by physicians. The memory 32 may be utilized only when a seizure event has been detected.

The AFE 16, classification processor 18, and optional patient specific treatment circuitry 20 will be described in more detail herein.

Analog Front End (AFE) 16

As noted above, the AFE 16 may include eight 2-channel DCCR AFEs for a total of 16 channels. For each 2-channel AFE, two input channels share an area-and-energy efficient DCCR CS-CCIA 22 followed by a corresponding PGA 26a, 26b. The DCCR CS-CCIA 22 achieves high input dynamic range, low noise and low power consumption to meet the strict design challenges of 50/60 Hz common-mode interference, in-band noise (including 1/f and Electrode DC Offset (EDO) of ~200 mV), and high electrode impedance (>100 MΩ) for a wearable environment.

Figure 3:
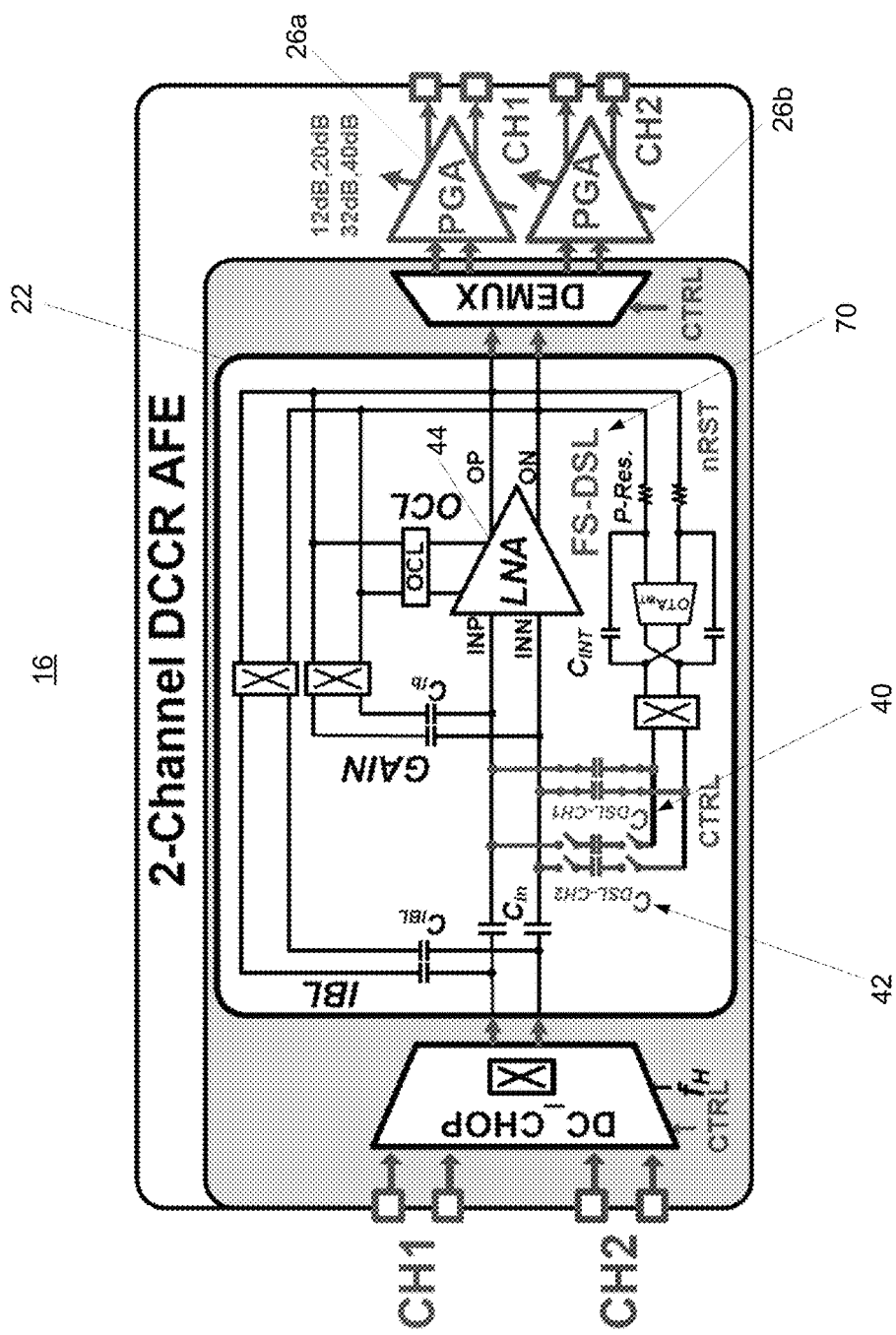
FIG. 3 generally illustrates a multi-channel (e.g., 16-channel) area- and-energy-efficient analog front-end (AFE) consistent with at least one embodiment of the present disclosure.
Figure 4:
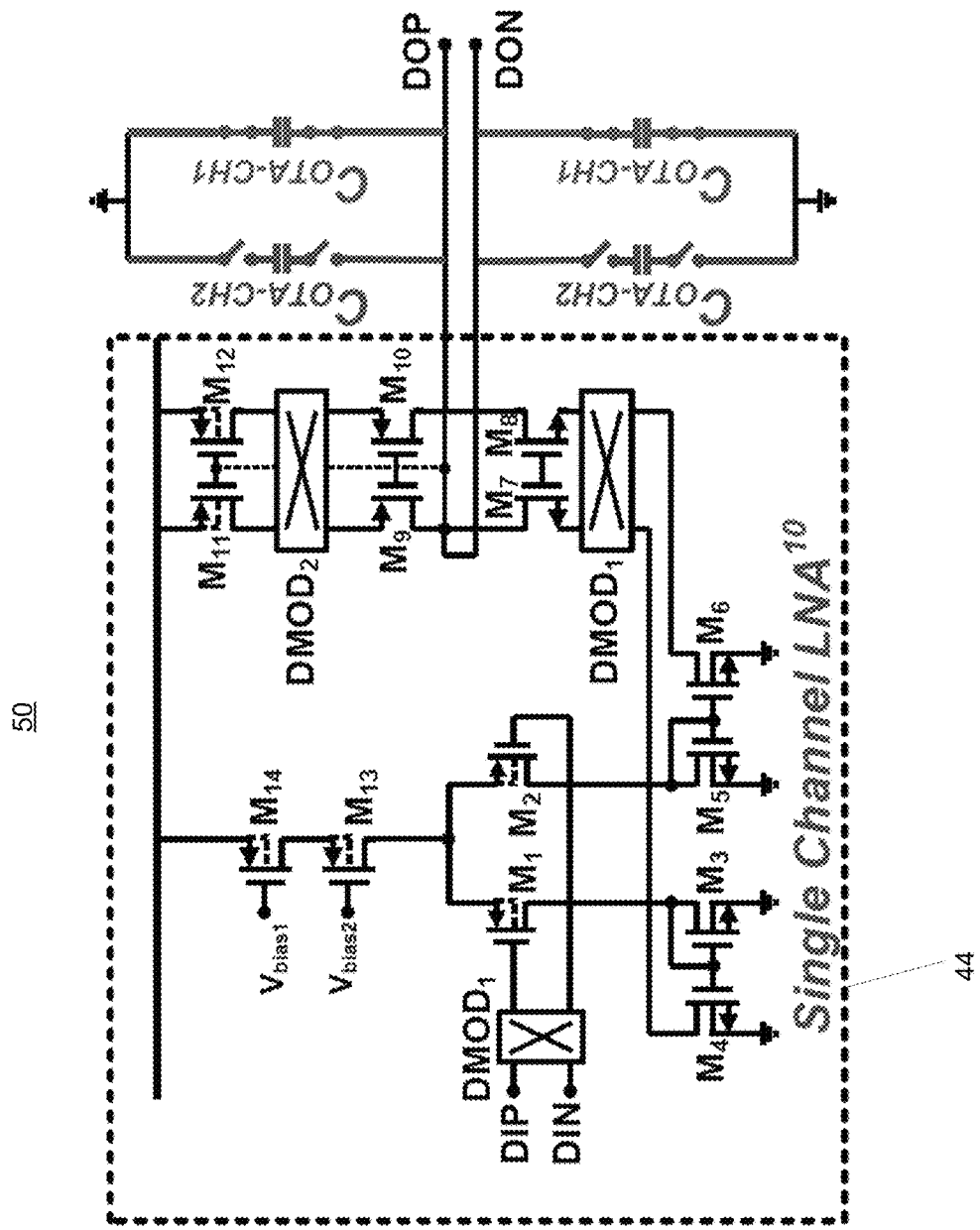
FIG. 4 generally illustrates a schematic of a LNA with intermediate node storage for DCCR CS-CCIA consistent with at least one embodiment of the present disclosure.

With reference to FIG. 3, one embodiment of a channel shared AFE 16 is generally illustrated. As an example of this embodiment, the following is shown for a two-channel inputs per amplifiers with 8 amplifiers resulting in 16-channels. Other embodiments are possible using a set of two or more channel inputs per amplifier. Further, two or more amplifiers are possible using each set of channel inputs. To minimize area and power consumption for the integration of 16-channels to meet the minimum technical requirement for clinical pediatric EEG standard and small form-factor for a patch sensor, every two-channel inputs CH1, CH2 of the DCCR-AFE 16 are time-multiplexed a DCCR CS-CCIA 22 followed by two PGAs that corresponds to each channel. When the CH1 is in amplification phase, the $C_{DSL-CH1}$ 40 is in sample mode and $C_{H2-CH2}$ 42 holds the previous voltage (analog sleep mode), and vice-versa. To ensure prompt and accurate switching between the two channels that have different EDO's, the last known internal Low Noise Amplifier (LNA) and DSL voltage values are stored in an intermediate nodes shown in the FIG. 3, on $C_{DSL-CH1}$ and $C_{DSL-CH2}$, for CH1 and CH2, respectively. It should be noted that due to the slew rate limitation of the IA 44, storing the intermediate value of the DSL itself may not be enough to ensure proper fast switching between the channels. Therefore, the 2-stage cascode LNA 50 (FIG. 4) also have $C_{OTA-CH1}$ and $C_{OTA-CH2}$ to store the intermediate bias value of CH1 and CH2, respectively. This reduces the stabilization time significantly from 61 µs to <40 µs to keep up with the channel switching speed. Both the sampling capacitors for the LNA 44 and the DSL are of value 1.5 pF, which results in maximum charge leakage of 10 fC during hold stage; this is less than 5% of the charge stored in the intermediate capacitor ($C_{DSL-CH1}$, $C_{DSL-CH2}$, $C_{OTA-CH1}$, and $C_{OTA-CH2}$) and is negligible.

Figure 5:
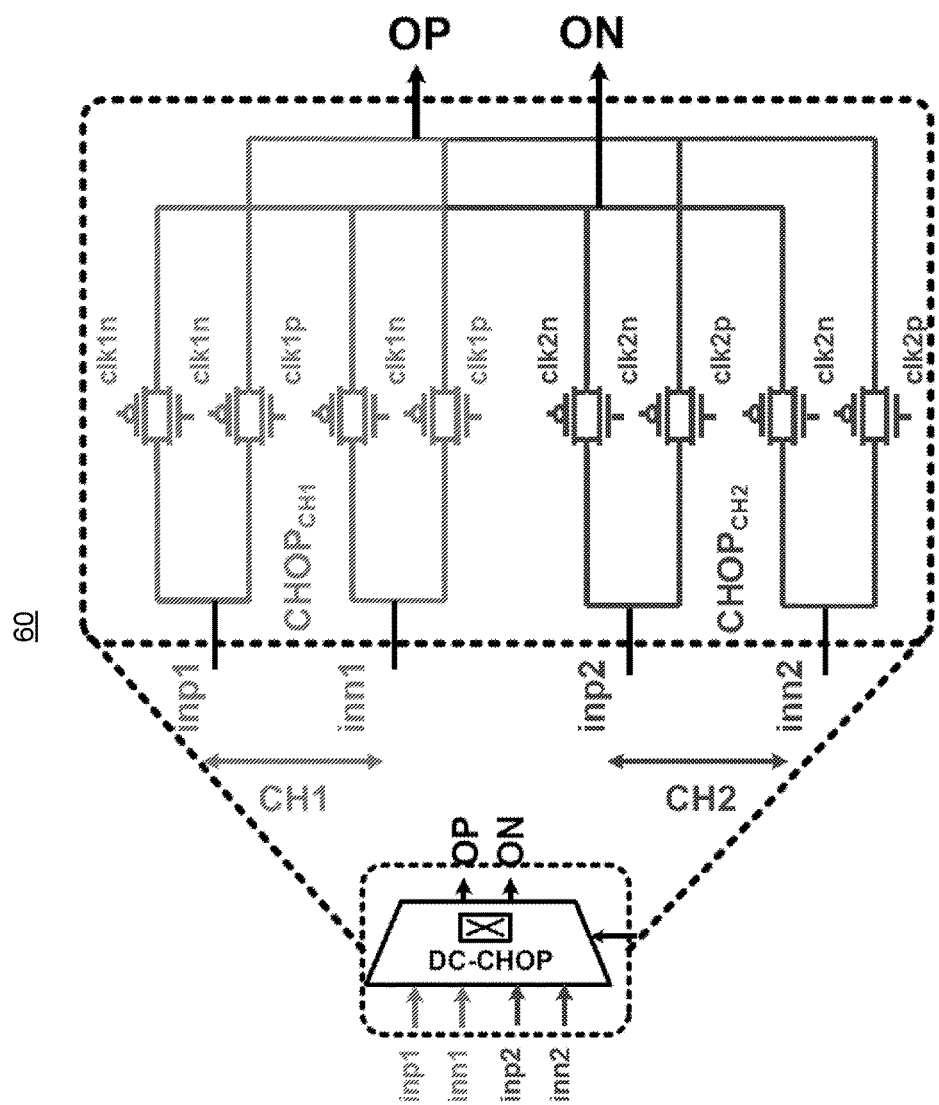
FIG. 5 generally illustrates a schematic of DC-CHOP structure consistent with at least one embodiment of the present disclosure.
Figure 6A:
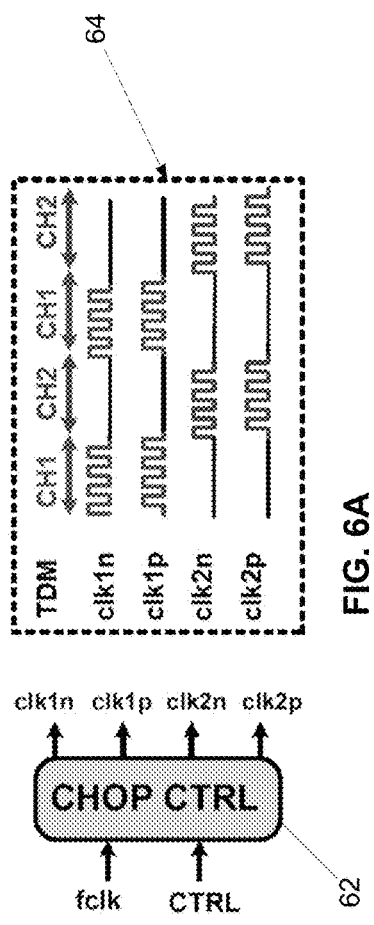
FIG. 6A generally illustrates a timing diagram for chopper control of the DC-CHOP consistent with at least one embodiment of the present disclosure.
Figure 6B:
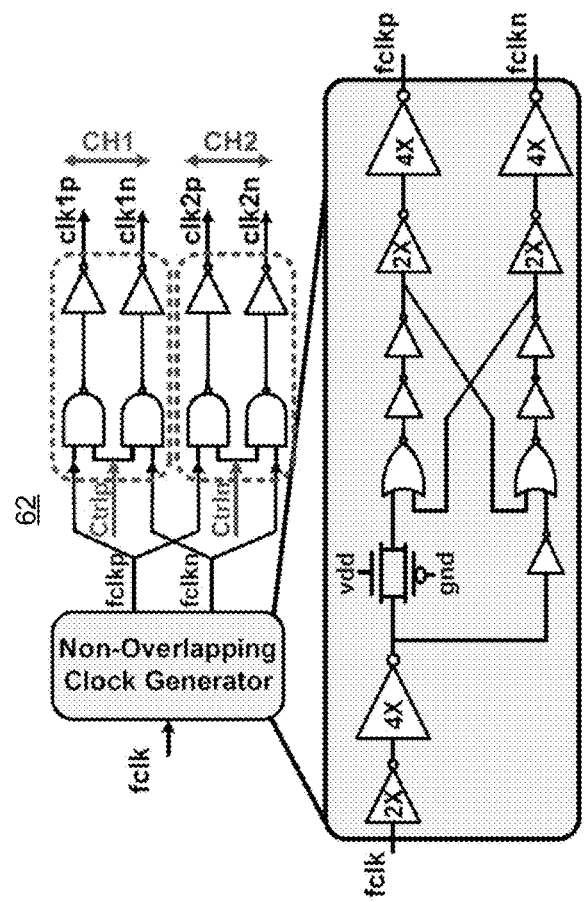
FIG. 6B generally illustrates an architecture for chopper control of the DC-CHOP consistent with at least one embodiment of the present disclosure.

Turning now to FIG. 5, one embodiment generally illustrating the schematic of Dual-Channel Chopper (DC-CHOP) 60 (see also, FIG. 2) that incorporates chopper switch and the channel mux function simultaneously is generally illustrated. The trade-off of the DC-DC-CHOP 60 comes at the expense of an adding a Time Division Multiplexing (TDM) chopper clock controller 62 (see, generally in FIG. 2) and a noise level elevation of 12%. One embodiment of the TDM chopper clock control waveform 64 and one embodiment of a schematic for the control wave generation 62 are generally illustrated in FIGS. 6A and 6B. The mathematical representation of DC-CHOP 60 in time and frequency domain is shown in equations (1)-(6) below. The time domain representation of 4 kHz chopping clock ($V_{4K}(t)$) and square pulse with ¼ k time period ($V_4(t)$) can be represented as follows:

$$V_{4K}(t) = \sum_{n=0}^{\infty} \left( V_{4\square}\left(t - n\left(\frac{1}{4000}\right)\right)\right) \quad (1)$$

$$V_4(t) = u(t) - u\left(t - \frac{1}{8000}\right) \quad (2)$$

where t is time in seconds and n varies from 1,2 ... ∞.

Fourier response of 4 kHz chopping clock ($V_{4K}(k)$) and 1 kHz chopper control clock ($V_{1K}(k)$) are then drawn as follows:

$$V_{4K}(k) = a_0 + \sum_{n=1}^{\infty} \left( \sin\frac{n\pi/2}{n\pi} \times \cos(8000\ \pi n) \times \left(k - \frac{1}{4}\right)\right) \quad (3)$$

-continued $$V_{1K}(k) = a_0 + \sum_{n=1}^{\infty} \left( \sin\frac{n\pi/2}{n\pi} \times \cos(2000\ \pi n) \times \left(k - \frac{1}{4}\right) \right) \quad (4)$$

where k and n varies from 1,2 . . . ∞.

The DC-CHOP 60 achieves multiplication between the chopping clock and the channel-control clock, V (t) shows the DC-CHOP multiplication result in equations (5) and (6).

$$V(t)=V_{4K}(t) \times V_{1K}(t) \quad (5)$$

$V(t)=\Sigma_{\downarrow}(n-0)^{\uparrow}(n-+\infty)\mathbb{K}\ V_{\downarrow}4(t-n(1/4000))\mathbb{J}$ for $n=\{2m,2m+1\}$ when $m$ is even $V(t)=0$ for $n=\{2m,2m+1\}$ when $m$ is odd (6)

where {2m,2m+1} represents {1st,2nd} index and m, n varies from 0,1,2 . . . ∞.

Figure 7:
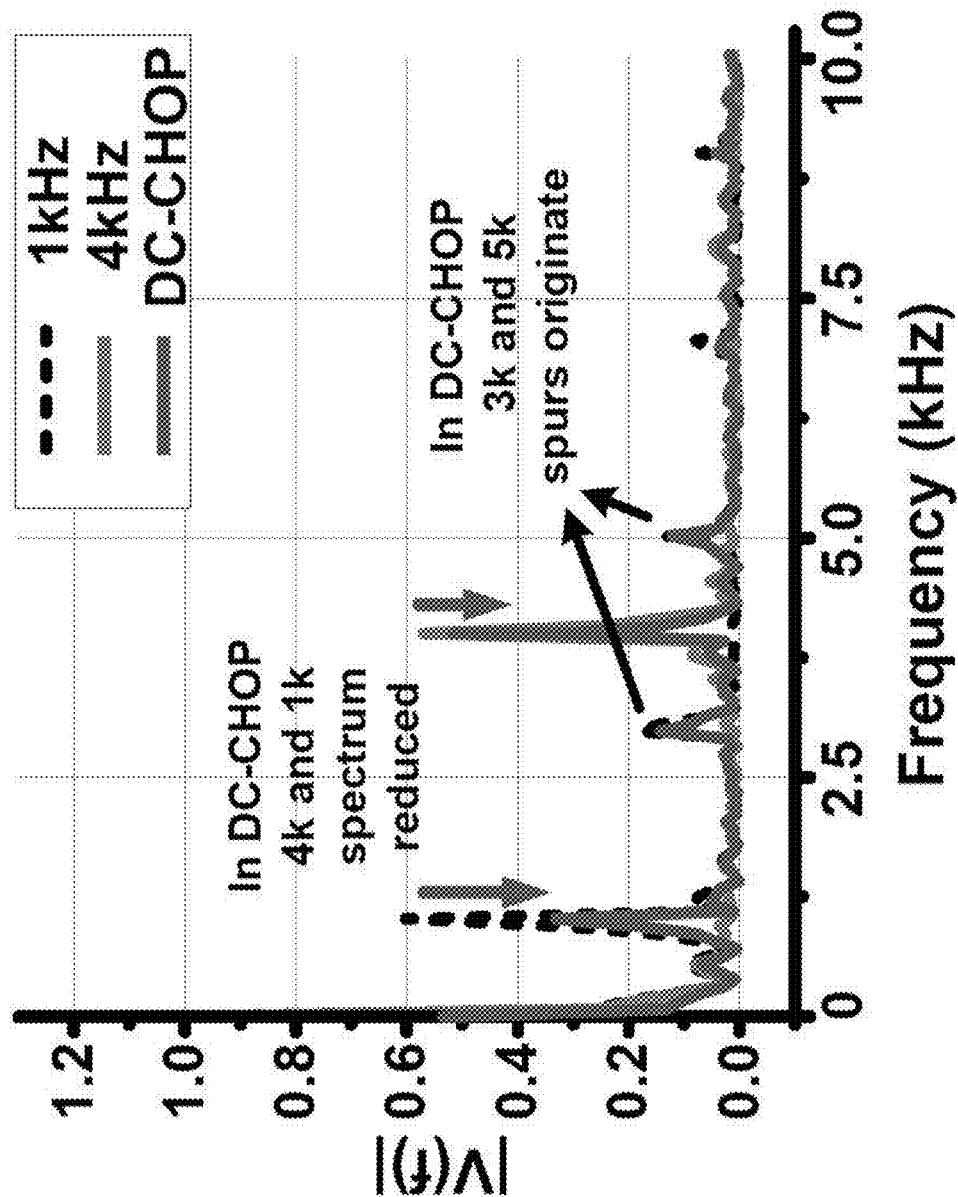
FIG. 7 generally illustrates a frequency domain analysis of a dual-channel chopper structure consistent with at least one embodiment of the present disclosure.

With reference to FIG. 7, the normalized frequency response of the input signal after chopping, denoted as normalized frequency response |V(f)| shows that the mixing of 1 kHz and 4 kHz induces small harmonics at 3 kHz and 5 kHz, but the spectrum of the signal component at 4 kHz is clearly distinguishable; the individual chopping channel functionality almost remain unaffected.

With reference back to FIG. 3, the AFE 16 also includes a DSL 70 including a sharp high-pass filter with near-DC high-pass corner (<0.5 Hz) to reject the EDO only. In contrast, known DSLs achieve such low frequency high-pass by introducing an extremely high loop impedance. However, due to the high loop impedance, the settling time at startup of known DSLs can reach up to several hours for EDO of ~240 mV. As may be appreciated, this makes a patch sensor very difficult to realize in practice. Even with storing intermediate voltage node values to overcome the variation between EDO's and slew rate issues, the DSL settling time still remains as a bottleneck to achieve fast switching between channels.

Figures 8A, 8B:
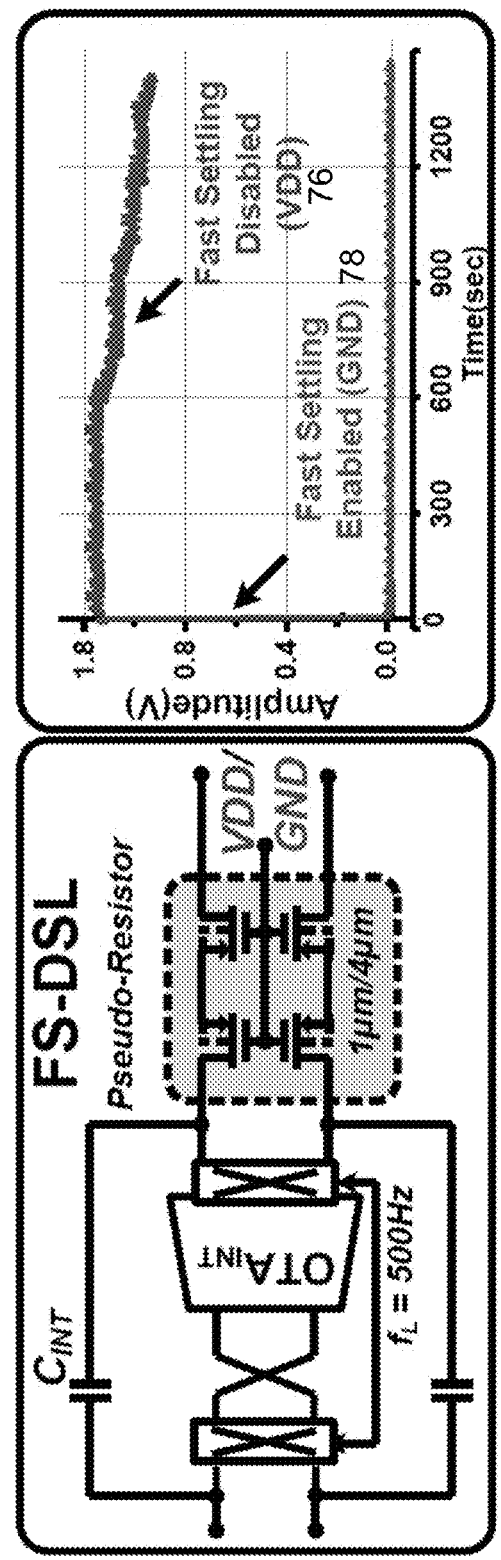
FIG. 8A generally illustrates a Fast Settling-DSL (FS-DSL) consistent with at least one embodiment of the present disclosure.
FIG. 8B generally illustrates FS-DSL measurement results (with FS disabled and FS enabled) consistent with at least one embodiment of the present disclosure.

In yet another embodiment, the AFE 16 may include the unique combination of pseudo-resistor (PMOS) acting as a register by connecting the PMOS gate with the system reset, nRST. When the nRST is engaged and the gate of the pseudo-resistor (PMOS) is connected to GND, it functions to temporarily reduce resistance of the pseudo-resistor until nRST is disengaged and is re-connected VDD. By doing so, this combination results in a surprisingly fast settling time of DSL, denoted as a Fast Settling-DSL (FS-DSL) 70, FIG. 8A. Compared to known DSLs, where the settling time of 1 s is achieved by adding an extra GM while consuming 7.4 µA/ch, the FS-DSL 70 of the present disclosure may settle within 0.5 s without any increased area or power consumption. Known DSLs cancel EDO through mixed signal DSL by implementing a digital Low-Pass-Filter (LPF), but are only able to cancel maximum EDO of 50 mV. The DSL settling measurement 74, FIG. 8B, shows when FS is disabled 76, setting time reaches over an hour. In contrast, when FS is enabled 78, the DSL settles within ~0.5 s for an EDO of 200 mV. Once the DSL settles, the FS will be disabled, at which point the switching glitch may lead to residual error; however, due to the high intrinsic capacitance of the DSL itself, the effect of such glitches is minimal. Also the FS-DSL 70 runs in a foreground manner, i.e. the normal operation will start after the FS. The time constant of LNA (τ) is calculated to be 8.7 us. Considering the 99.9% settling time, which is equivalent to 61 us (6.9×τ), the Correlated Double Sampling (CDS) based PGA 44 samples at 8 kHz and the DC-CHOP 60 switches at 1 kHz, which is exactly the double of the chopping frequency (4 kHz) and the quadruple of the switching frequency, respectively. Hence, the PGA 44 samples its data after the input has sufficiently settled to ensure correct sampling. The relation between these frequencies has the advantage of mitigating residual offset caused by the charge injection due to channel switching in addition to the chopper switch.

The DCCR CS-CCIA 22 of the present disclosure recycles the bias current between the two channels CH1, CH2 to decrease the effective current consumption by 43% (0.9 µA/ch) and area by 28% compared to known CS-CCIA, while also elevating the integrated input referred noise level at 1-100 Hz by only 12%.

Classification Processor 18

With reference back to FIG. 2, the SoC 10 also includes a classification processor 18. The digitized data is received from the AFE 16 and is processed by the classification processor 18 (e.g., a Dual-Detector Architecture ($D^2A$) classification processor) that is comprised of Frequency-Time Division Multiplexing (FTDM) Feature Extraction (FE) engine 28 followed by the $D^2A$-Linear Support Vector Machine (LSVM) engine 30. The dual LSVM classifier 18 enhances both sensitivity and specificity at once by implementing a digital hysteresis.

In order to achieve high sensitivity (>95%) and specificity (>97%) in seizure onset and termination detection, the $D^2A$ classification processor 18 utilizes SVM-based machine learning algorithm to support patient-to-patient and age-to-age variations. Energy efficient fully and partially autonomous SVM classifiers have been previously presented for generic and biomedical applications, however, high classification accuracy and small latency requirement for seizure detection makes them difficult to be used in this design.

Figure 9:
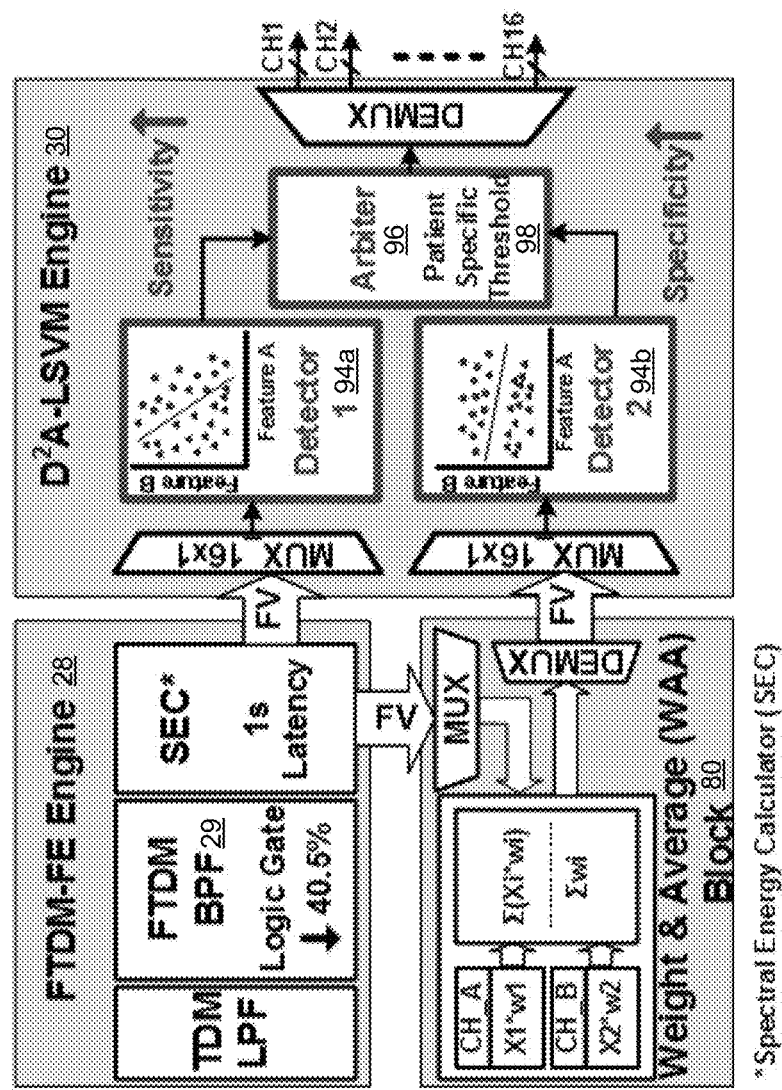
FIG. 9 generally illustrates a block diagram of a $D^2A$ classification processor consistent with at least one embodiment of the present disclosure.

One embodiment of the $D^2A$ classification processor 18 is illustrated in more detail in FIG. 9. The $D^2A$ classification processor 18 may include a FTDM-FE engine 28 to extract Feature Vectors (FVs), a Weight-And-Average (WAA) block 80 to enhance seizure termination detection, and a $D^2A$-LSVM engine 30 to determine beginning and end of seizure.

Frequency-Time Division Multiplexing (FTDM)-Feature Extraction (FE) Engine 28

As an example, the implemented $D^2A$ classification processor 18 processed 16-channels for its Feature Extraction (FE), where each FE channel is comprised of seven filter banks (46-tap) increased the number of required filter banks to 112 thereby significantly increasing the amount of area as well as hardware resource or power. If one recognizes in this example, the 16-channels per FE may be 24-channels or x-channels higher, the area and power consumption additional. While the following description is provided based on 16 channels, it should be appreciated that the FTDM-FE 28 is not limited to 16 channels (unless specifically claimed as such), and that the FTDM-FE 28 may process less than, or greater than, 16 channels. A person of ordinary skill in the art would, based on the present disclosure, understand any modifications necessary to the FTDM-FE 28 to process less than, or greater than, 16 channels.

Figures 10A, 10B:
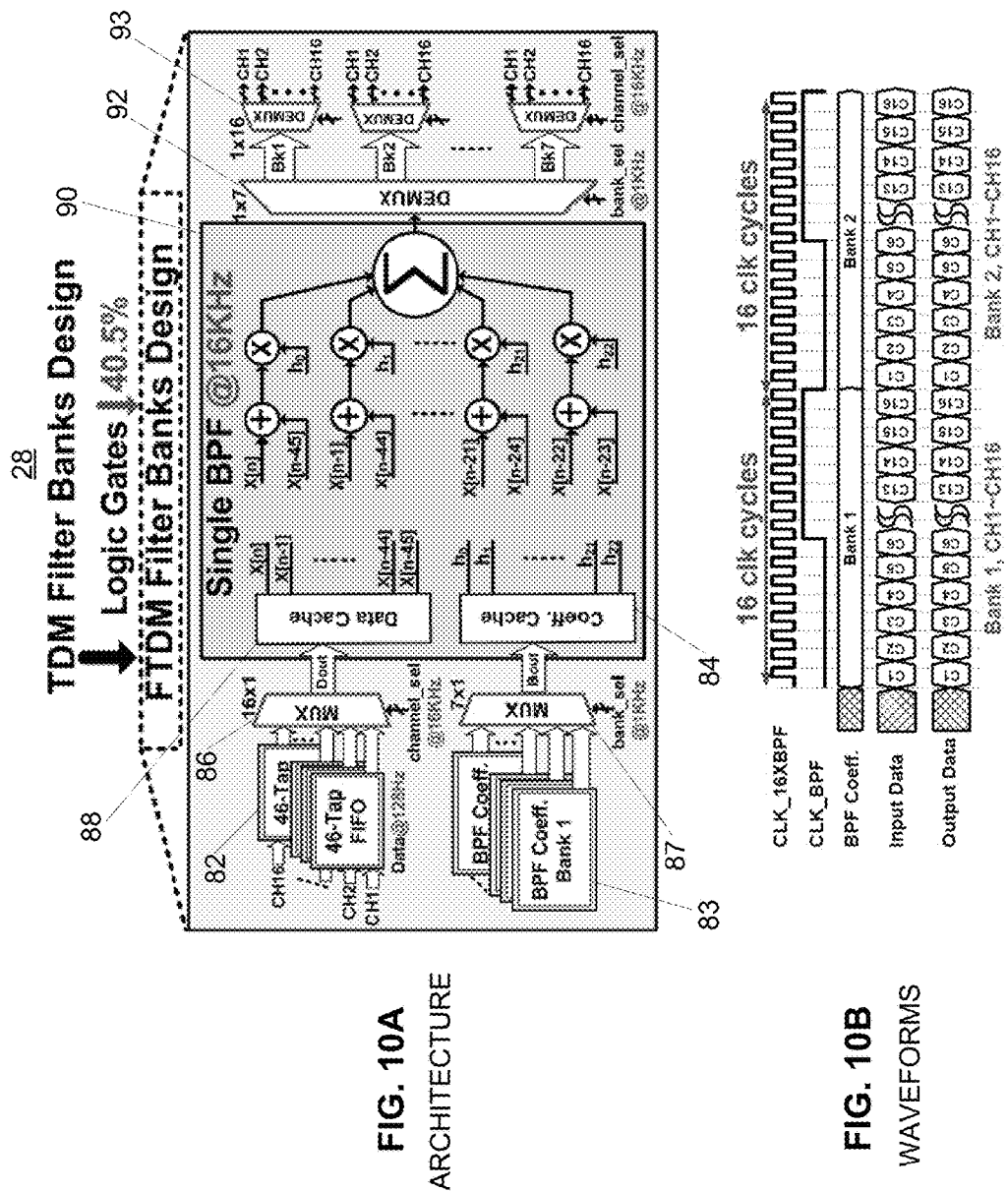
FIG. 10A generally illustrates a FTDM-BPF architecture consistent with at least one embodiment of the present disclosure.
FIG. 10B generally illustrates a timing diagram consistent with at least one embodiment of the present disclosure.

In another embodiment, the FTDM-FE engine 28 multiplexes one BPF where an individual filter bank corresponds to a specific frequency band, which may vary depending use in bandwidth. As generally illustrated in FIG. 10A, by using a plurality of bandwidths, a multiple number of filter banks (BPF) can be processed resulting in frequency multiplexing of filter banks, unexpectedly reducing both power consumption and area required. A further embodiment is incorporating the timing element of channel samples into filter bank which allows multiple channel samples to be processed through a single filter bank, by further reducing the power consumption and area.

With further reference to FIG. 10, one embodiment of the architecture of the FTDM-FE engine 28 along with a timing diagram is generally illustrated. Input data for 16 channels (CH1 . . . CH16) are stored in parallel in 16×46-tap FIFOs 82, e.g., but not limited to, at 128 sample/s. BPF coefficients for 7 BPF banks 83 are multiplexed into coefficients cache 84, e.g., but not limited to, at 1028 Hz. The data for the 16-channels data in FIFOs 82 are multiplexed (e.g., using 16×1 MUX 86) into data cache 88 of a single BPF 90 (e.g., but not limited to, at 16 kHz) to calculate outputs of one specific bank for all 16 channels. It is then de-multiplexed (e.g., using DEMUX 92) to corresponding banks in each channel.

Compared with known TDM-BPF, the FTDM-BPF 28 only utilizes 16×46-tap FIFOs 82, 7 BPF coefficients register groups 83, and a single 46-tap BPF 90 at 16 kHz to process FE for 16 channels CH1 . . . CH16. This design shrinks the gate number of the FE engine by 57.6% and 40.5% compared with 16-channel Distributed Quad-LUT (DQ-LUT) and 16-channel TDM-BPF, respectively. The FTDM 28 may utilize a maximum operation frequency of the single BPF 90 from 1 kHz to 16 kHz, which is acceptable in this scenario.

Figure 11:
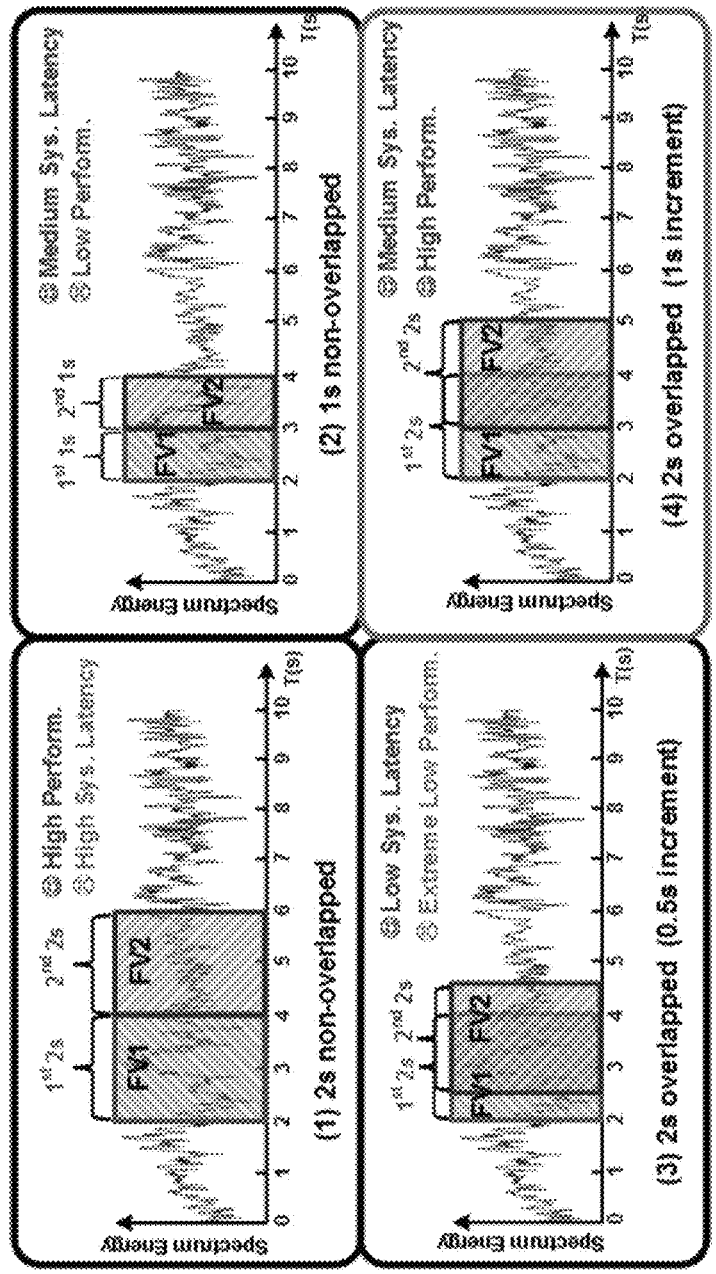
FIG. 11 generally illustrates a window technique comparison consistent with at least one embodiment of the present disclosure.

Apart from the precise detection and 16-channel integration, it may be desirable for the SoC 10 to have low latency to suppress the abnormal activity during the electrical onset duration, which is achieved by small latency of 1 s in FE 28. It is desirable to have low latency because electrical onset typically prevails the clinical onset by 10-30 s in many patients. Four configurations of epoch windowing design have been analyzed to achieve the best trade-off between performance and system latency: #1 2 s non-overlapped window; #2 1 s non-overlapped window; #3 2 s overlapped window with 0.5 s increment; and #4 2 s overlapped window with 1 s increment. Simulation results reveal that #1 (2 s non-overlapped window) has the best performance while longest system latency; #2 (is non-overlapped window) and #3 (2 s overlapped window with 0.5 s increment) have small latency of 1s and 0.5 s, respectively, but suffer from performance loss; and #4 (2 s overlapped window with 1 s increment) achieves smallest system latency without compromising the performance. FIG. 11 summarizes the comparison of pros and cons of above-mentioned windowing techniques. The proposed design #4 (2 s overlapped window with 1 s increment), in which the last 1 s spectral energy information of current FV is shared with the next FV, overcomes the issue of 2 s non-overlapped windows and make the system more robust.

Weight-And-Average (WAA) Block 80

In order to also detect the end of seizure, the SoC 10 (e.g., the classification processor 18) may include a WAA block or algorithm 80. The WAA 80 assigns weights to each channel and recalculates the FVs based on these weights. Channels with greater spectral energy difference will be assigned with larger weights, thus biasing the recalculated spectral energy information towards these channels. This can incorporate spatial information without being overly sensitive to spatial shifts in ictal and postictal activity and provide more accurate seizure termination detection.

The application of WAA to all EEG channels (with 15 sub-banks per channel) presented several problems. For example, this approach requires considerable hardware and power overhead. In addition, seizure patterns from same the patient may differ from channel to channel; an exemplary case is a patient having secondarily generalized seizures and localized seizures at the same time, in which case it is difficult to find multiple channels with same or similar seizure patterns. Moreover, it may even bring down the classification accuracy if localized seizures are involved. To overcome these issues, the classification processor 18 of the present disclosure only adopts the WAA for every two adjacent channels (for a total of 8 pairs), which improves the performance and decreases the hardware overhead simultaneously and significantly. Compared to the prior WAA systems, the WAA 80 of the present disclosure reduces the gate count and energy consumption by 56% and 23%, respectively.

$D^2$A-LSVM Engine 30 with Digital Hysteresis

To achieve high accuracy for seizure onset and termination detection, the $D^2$A-LSVM engine 30, FIG. 9, a unique digital hysteresis design is generally illustrated which may be implemented using two LSVM detectors 94a, 94b that operate simultaneously, with one detector optimized to sensitivity and the second optimized to specificity. Detector-1 94a may be trained for sensitivity (e.g., by carefully decreasing penalty parameter "box-constraint" within the range of $[10^{-4}, 10]$), whereas as Detector-2 94b, along with WAA 80, may be trained for specificity (e.g., by carefully increasing penalty parameter "box-constraint" within the range of $[10^{-4}, 10]$). Both detectors 94a, 94b may be based on an area efficient LSVM with condensed training (e.g., but not limited to, by using "autoscale" function from Bioinformatics Toolbox), which centers the training samples at their mean and scales them to have unit standard deviation before training, hence allowing expanding training set from 160 s to ~2500 s with more non-seizure patterns. Adding more non-seizure patterns in training can significantly improve the classification accuracy of LSVM. It should be appreciated, however, that the engine 30 is not limited to only LSVM, and that other techniques may be used.

The new decision equation is then amended as in (7) and (8):

$$\text{Seizure:} W^{T*}[\text{scaleFactor}*(X+\text{scaleShift})]+\beta>0 \quad (7)$$

$$\text{Nonsizure:} W^{T*}[\text{scaleFactor}*(X+\text{scaleShift})]+\beta<0 \quad (8)$$

Where W, β, scaleFactor, scaleShift are patient specific parameters derived from training phase; X is the extracted FV. More specifically, the scaleFactor is the reciprocal of the standard deviation of training samples and the scaleShift is the mean of the training samples. LSVM is less computationally expensive than linear regression ($O(mN^2)$ versus $O(N^3)$, where m is the number of support vectors). SVM's (including LSVM) low hardware complexity is more suitable to reduce the power consumption for long term continuous monitoring system. While Non-Linear SVM (NLSVM) may have better classification performance over LSVM, this is subject to the availability of sufficient number of seizure patterns and support vectors from a single patient. In practice, however, the amount of available seizure patterns from one individual is usually very limited, especially for those patients who only have occasional seizure every several days or even months. In addition, one individual may undergo several different types of seizure patterns. For instance, the patient may experience secondarily generalized seizures or localized seizures that occur less frequently than the patient's usual seizure patterns. These types of seizure patterns' spatial and spectral structures can be very different from those of the seizures we use for training. Consequently, the use of nonlinear boundaries that tightly fit the distribution of the training samples may result in poor performance on seizures not well represented by the training data. On the contrary, in such limited training set environment, the LSVM may have better classification accuracy over NLSVM with less training sets as it does not tightly circumscribe the training vectors, which will give more tolerance margin for test seizures that appear much different than the training ones.

Figure 12:
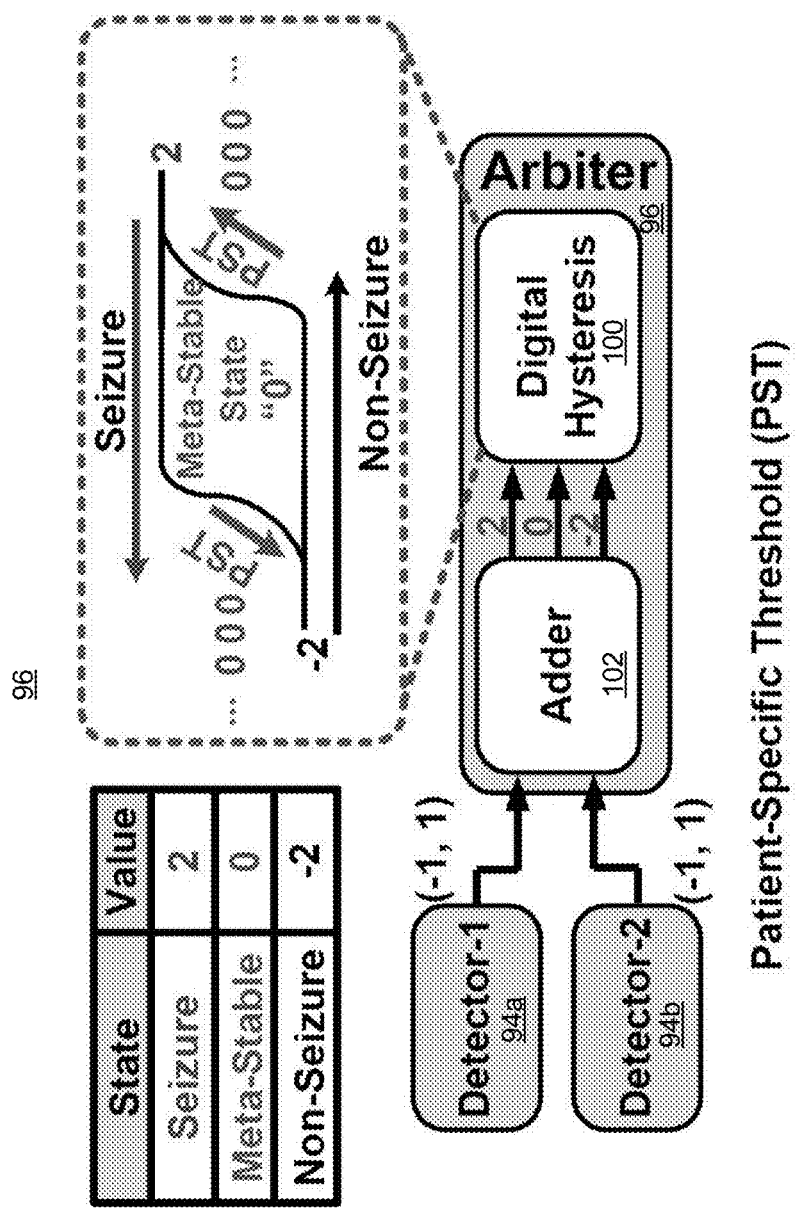
FIG. 12 generally illustrates an arbiter architecture consistent with at least one embodiment of the present disclosure.
Figure 13:
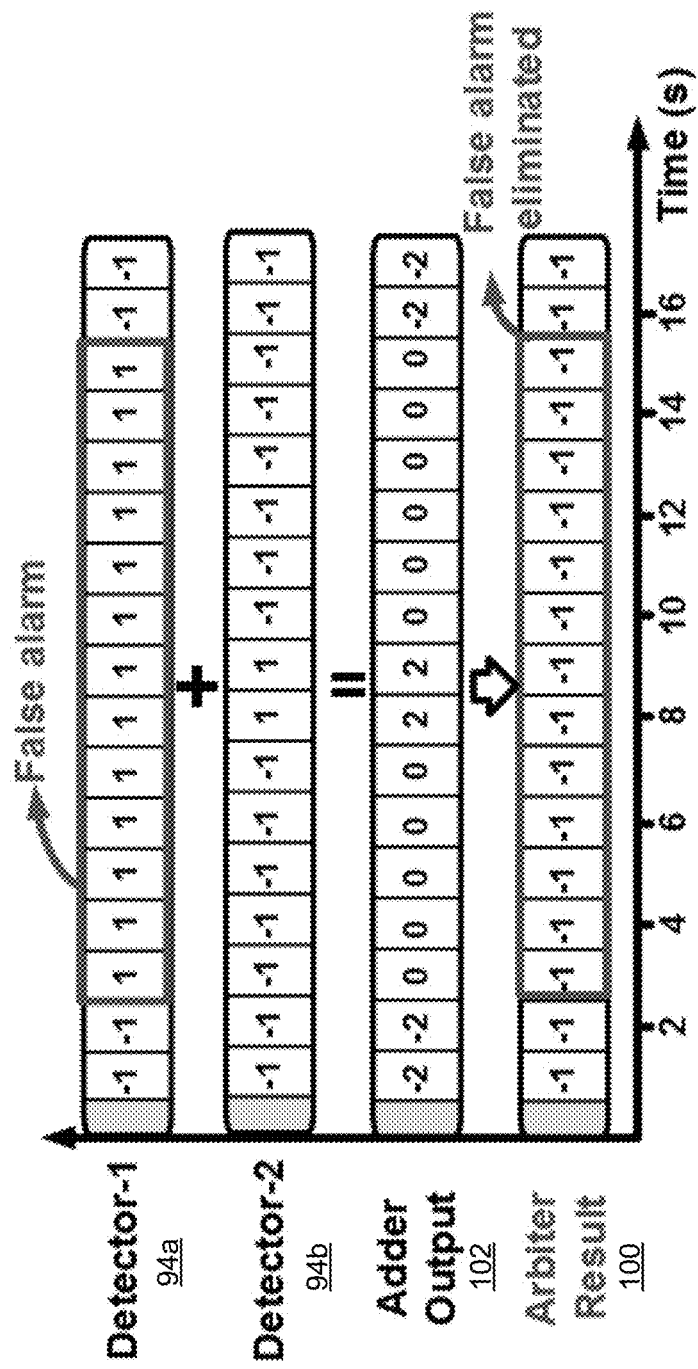
FIG. 13 generally illustrates an example of digital hysteresis implementation consistent with at least one embodiment of the present disclosure.

To improve the performance of the SoC 10 even further, the classification processor 18 may optionally include an arbiter 96 with digital hysteresis that contains a Patient Specific Threshold (PST) 98, established by supervised learning or obtained using a self-learning algorithm. Turning now to FIG. 12, one embodiment generally illustrating the architecture of arbiter 96 is generally illustrated. The arbiter 96 yields new classification results as the sum of output from the two LSVM seizure detectors 94a, 94b, which is defined as: a) seizure (2); b) non-seizure (−2); and metastable (0) states as listed in FIG. 12. Metastable in seizure state is considered as seizure, while metastable in non-seizure state is considered as non-seizure. PST is introduced to specify the condition of transiting from one state to the other. When PST continuous seizures have been detected in non-seizure state, $D^2$A-LSVM engine 30 will transit to seizure state, and vice versa. FIG. 13 shows one example of a proposed digital hysteresis eliminating false alarms during non-seizure scenario from EEG database. Assuming PST of 3, detector-1 94a undergoes a false alarm lasting for 13 s. This false alarm can be eliminated by setting PST to 14 s. However, the interval between seizure electrical onset and clinical onset may vary from 0.5 s to 10 s, with the median value of 3 s, hence this is unacceptable as the detector only declares a seizure onset after 14 s of the correct time stamp. In detector-2 94b with WAA 80 applied, the false alarm duration is significantly reduced from 13 s to 2 s. By applying digital hysteresis 100 to the output of the adder 102, the false alarm is eliminated as shown in FIG. 13. Since the number of continuous seizure samples (e.g., 2) is under the PST value, current state will not transit from normal to seizure. Similarly, same procedure applies for eliminating false negatives.

Patient Specific Treatment Circuitry 20

With reference to FIG. 2, the SoC 10 may optionally include patient specific treatment circuitry 20. For example, the patient specific treatment circuitry 20 may include transcranial electrical stimulation (tES). One example of tES includes, but is not limited to, Patient Specific Voltage Mode Non-Invasive TES as described herein. The embodiments herein could be used in the number of applications using electrical signals in conjunction with the skin-electrode impedance monitoring to treat subjects, either human or animals, having a variety of biological conditions and diseases. A unique feature of skin-electrode impedance monitoring is absence of the requirement for having a dedicated current injecting circuitry.

Many neural and psychiatric abnormalities are associated with clinically detectable, altered brain dynamics. The aberrant brain activity can be restored through electrical stimulation. In epilepsy, seizure patterns emerge intermittently. As a result, a closed-loop brain control that leaves other aspects of brain functions unaffected is desirable. tES uses direct electrical currents from surface to stimulate specific parts of the brain. A constant, low intensity current is passed through two electrodes placed over the head which modulates neuronal activity. Although tES is still an experimental form of brain stimulation, it potentially has several advantages over other brain stimulation techniques: it is non-invasive, inexpensive, painless and safe. Minimal side effect of tES is a slight itching or tingling on the scalp.

tES can be further divided into 3-types based on the mode of stimulation: #1 Current-Mode Stimulation (CMS), #2 Voltage Mode Stimulation (VMS) and #3 Charge-Mode Stimulation. CMS is less power efficient compared to VMS because an on-chip current source is needed to ensure constant current delivery. Known systems that incorporate tES for mental health management consume 32 µA-2 mA based on the current mirror circuit but do not take into account impedance variation and charge balancing. Other systems uses additional Differential Sinusoidal Current Stimulator (DSCS) and pseudo sinusoidal current source to inject constant current, respectively, at the cost of high power consumption (>18 µW). With reference to FIG. 14, a major drawback of known VMS is the skin impedance variation 1) due to motion artifacts, 2) between the patients and 3) during the stimulation duration within a patient that makes it very difficult to ensure constant charge delivery.

Figure 15:
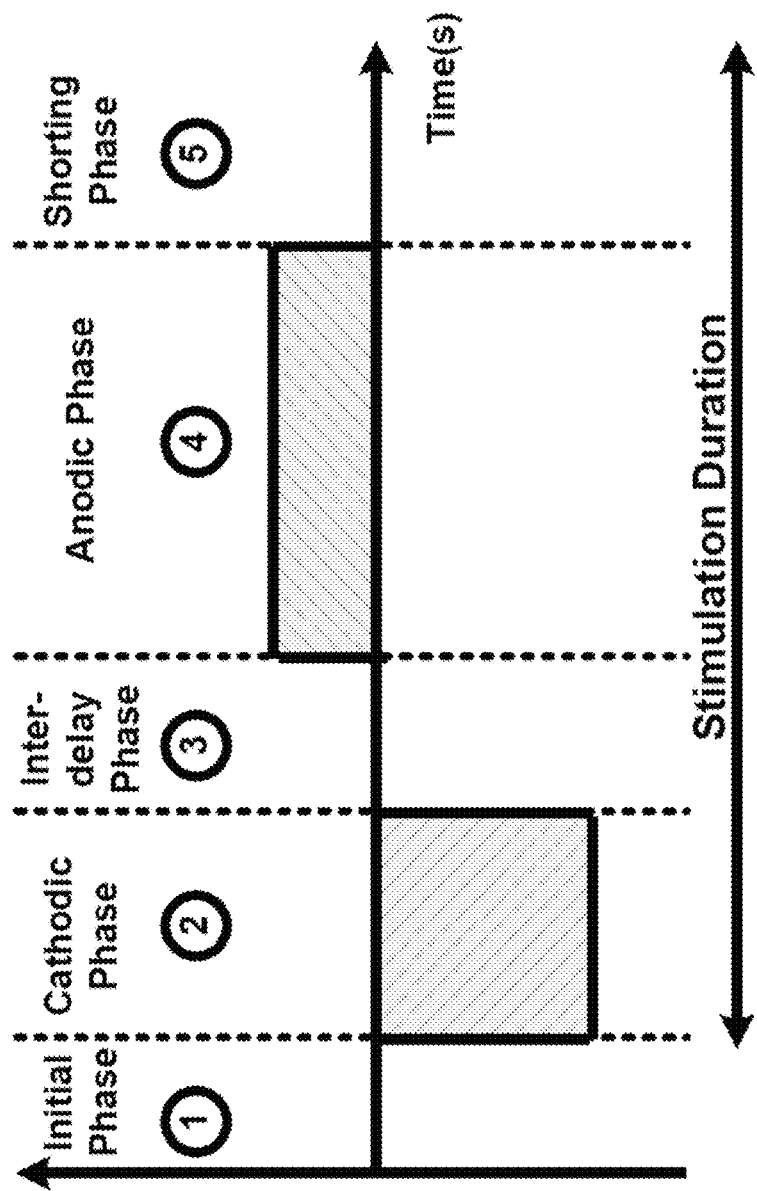
FIG. 15 generally illustrates biphasic stimulation pattern to ensure patient-safety with no-net charge accumulation consistent with at least one embodiment of the present disclosure.

To ensure patient safety and to avoid tissue damage, the patient specific treatment circuitry (e.g., PVTES) 20 of the instant disclosure may feature bi-phasic stimulation. As generally illustrated in FIG. 15, the bi-phasic stimulation of the PVTES 20 delivers a charge in cathodic phase that is retrieved back in anodic phasic with an inter-phase delay, therefore no-net charge is accumulated in the body.

Figure 16:
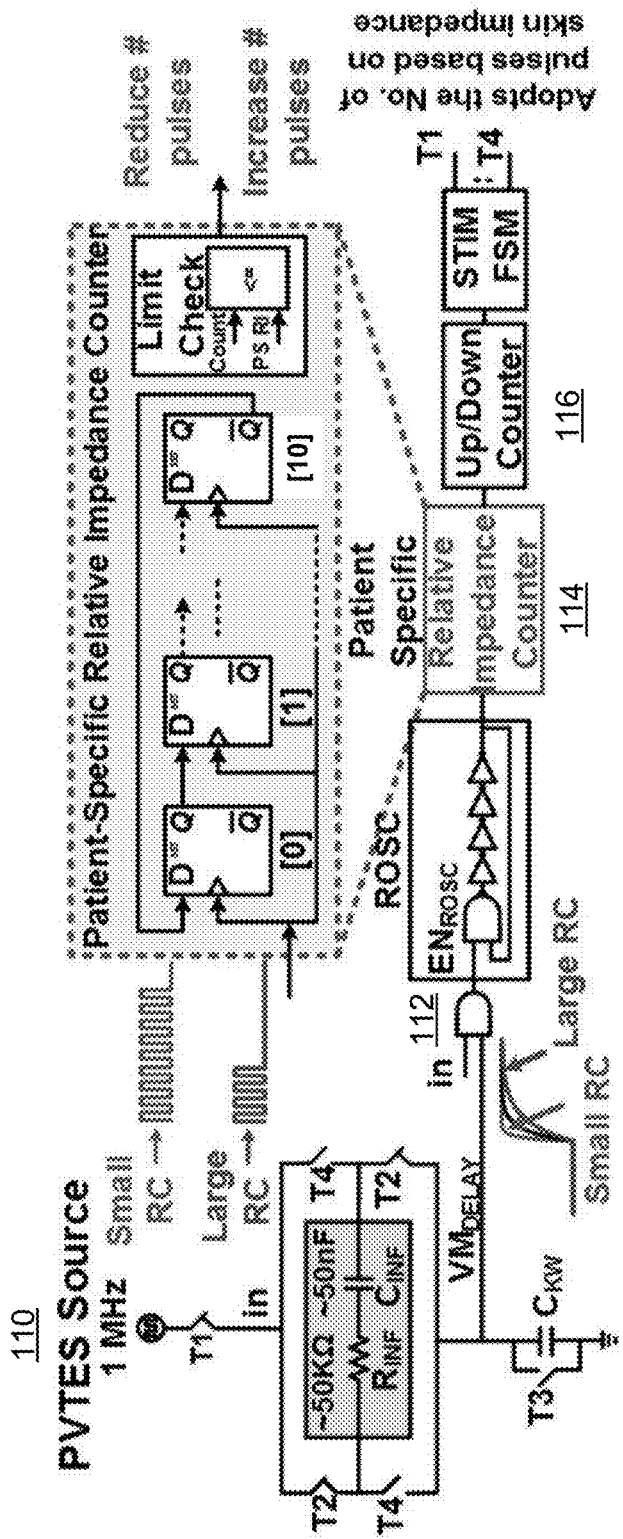
FIG. 16 generally illustrates a patient specific tES for epileptic patients with on-chip impedance adaptive control consistent with at least one embodiment of the present disclosure.

Turning now to FIG. 16, one embodiment generally illustrating PVTES 20 with on-chip impedance adaptive control is generally illustrated. The PVTES 20 can adapt to skin-electrode resistance and capacitive value ranging from 2-200 kΩ and 10-100 nF, respectively, to overcome the major drawback of conventional VMS. The stimulation source 110 may be a 1 MHz voltage-mode pulse, where number of pulses can be controlled by different RC time constant formed by the tES circuit and the skin-electrode impedance. VM_delay is an RC relaxed version of the input VMS coming after passing through the human scalp and known capacitor ($C_{KW}$). The $C_{KW}$ value may be selected to be 5 pF, which is <1/100 of the interface capacitance ($C_{INF}$), such that the 5 pF will be the dominated. The output of the AND gate ($EN_{ROSC}$) 112 will reflect the value of the skin-electrode impedance by changing the ON-time period. If the $R_{INF}$ has a large value, then $EN_{ROSC}$ will be ON for less time and vice-versa for smaller $R_{INF}$. In order to evaluate the value of $R_{INF}$, a 10b counter 114 is used to count during the ON period of the $EN_{ROSC}$. The speed of the clock for the 10b counter 114 should be sufficiently higher than VMS (e.g., 1 MHz) clock source such that a small difference in the ON period can be detected. A Ring Oscillator (ROSC) may be used to generate a clock signal with frequency >50 MHz that will be used by the counter. The 10b counter 114 runs until the stimulation pulse reaches to the desired value ($V_{STIM}$ for a cathodic phase, and GND for an anodic phase); the resulting counter value reflects the current skin-electrode impedance value (the higher counter value, the higher impedance). This counter value will decide the number of the stimulating pulses to be applied to the patient. The counter 116 counts up to its loaded value during the cathodic phase and counts down from its loaded value to zero in the anodic phase. The same 10b counter 114 may be utilized for both impedance monitoring using RC relaxation, and charge balancing (for cathodic and anodic phase) to remove any residual charge. Also, the PVTES 20 achieves low power implementation (2.45 µW) compared other systems and there is no need for an additional current injection to monitor skin-electrode impedance.

Implementation and Measurement Results

Figures 17A, 17B:
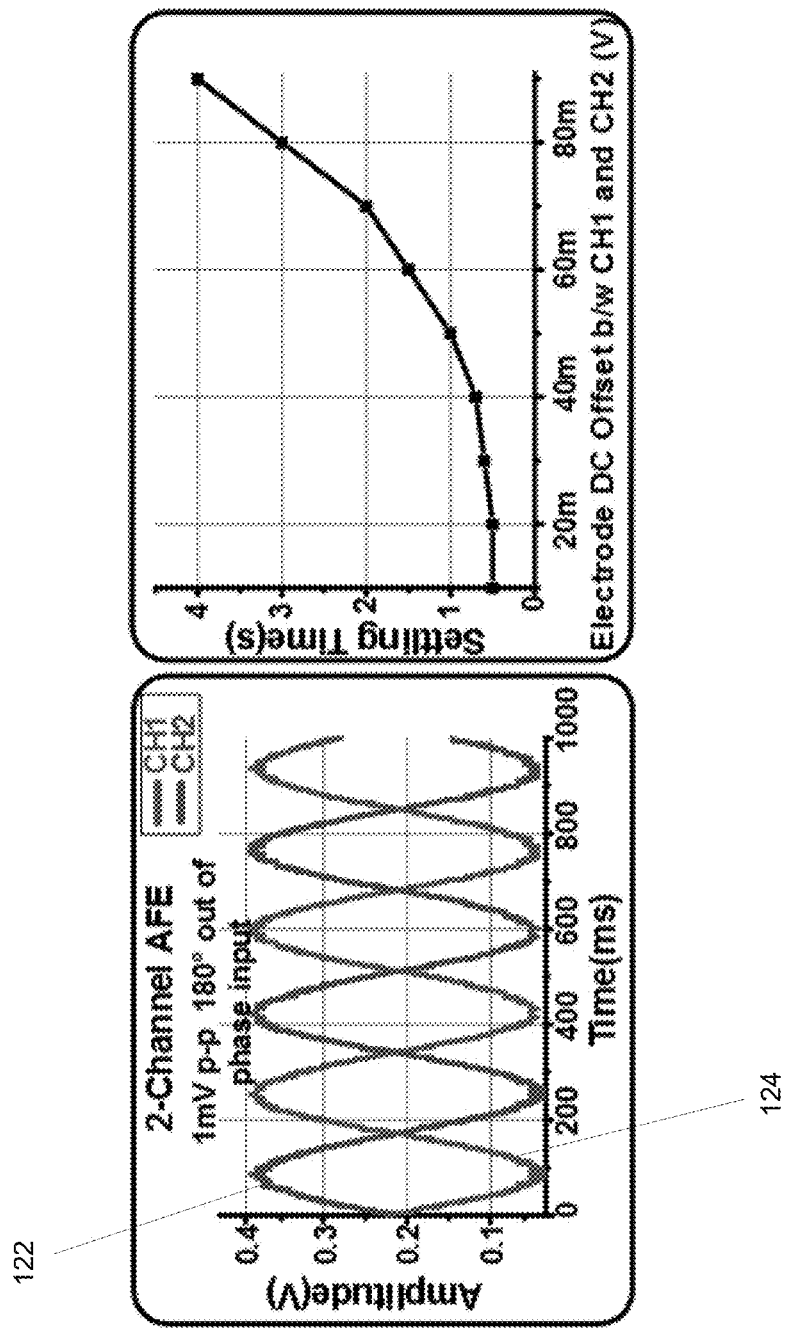
FIG. 17A generally illustrates measurement results of two channel operation of the DCCR-AFE with a worse case 180 degree out-of-phase input consistent with at least one embodiment of the present disclosure.
FIG. 17B generally illustrates measurement results of two channel operation of the DCCR-AFE with a worse case 180 degree out-of-phase input consistent with at least one embodiment of the present disclosure.
Figure 18B:
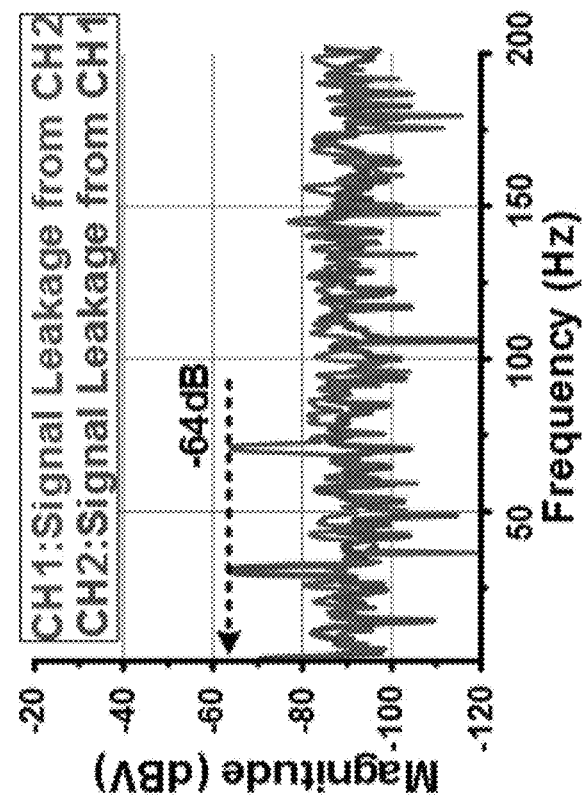
FIG. 18B generally illustrates measured small signal leakage between CH1 and CH2 consistent with at least one embodiment of the present disclosure.
Figure 18A:
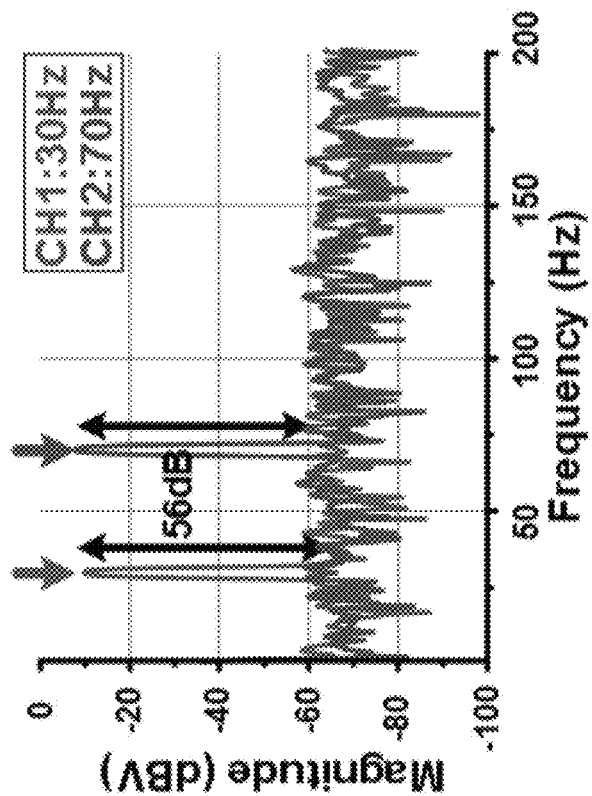
FIG. 18A generally illustrates measured crosstalk between CH1 and CH2 consistent with at least one embodiment of the present disclosure.

Turning now to FIG. 17A, one embodiment of the DCCR-AFE measurement results is generally illustrated. A pair of 180° out-of-phase sine inputs 122, 124 are applied for each channel, which is the one of the worst case scenario in terms of settling. The measured output from the PGA 44 of specific channel set at the gain level of 12 dB confirms the proper signal amplification of 52 dB per channel (1 mV, 180° out-of-phase signals amplifying to corresponding 300 mV outputs). The performance of DCCR CS-CCIA 22 was also verified with EDO difference of 20 mV, 40 mV and 80 mV between CH1 and CH2, as shown in FIG. 17B. FIG. 18 show the measured crosstalk with an average of −56 dB. In particular, FIG. 18A shows the measured outputs when 2 signals at 30 Hz and 70 Hz are applied to CH1 and CH2, respectively. When monitoring CH1 alone (FIG. 18B), the small signal leakage from CH2 at 70 Hz is observed and vice-versa for CH2. The signal leakage from CH1 to CH2 and CH2 to CH1 is at −64 dB, while the signal amplitude is at −8 dB; the crosstalk is around −56 dB.

Figure 19B:
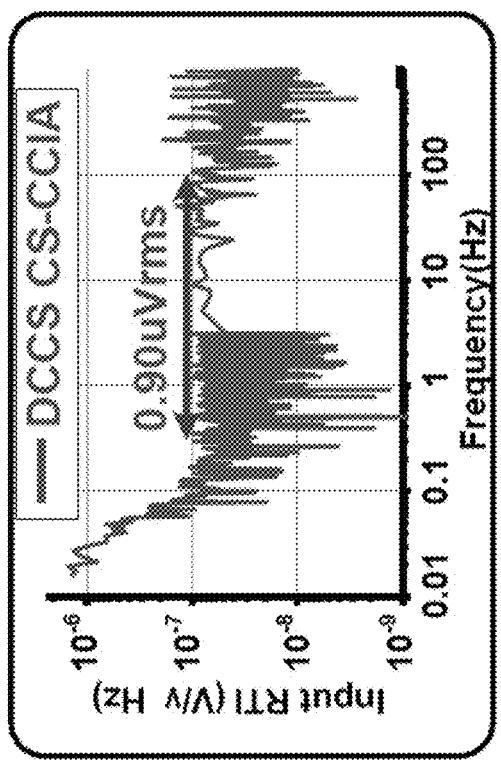
FIG. 19B generally illustrates measured RTI of the DCCR CS-CCIA consistent with at least one embodiment of the present disclosure.
Figure 19A:
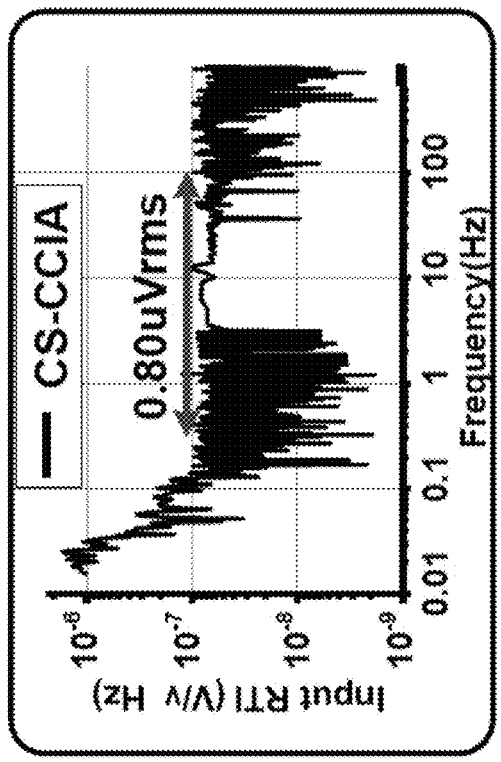
FIG. 19A generally illustrates measured RTI of the CS-CCIA consistent with at least one embodiment of the present disclosure.
Figure 20:
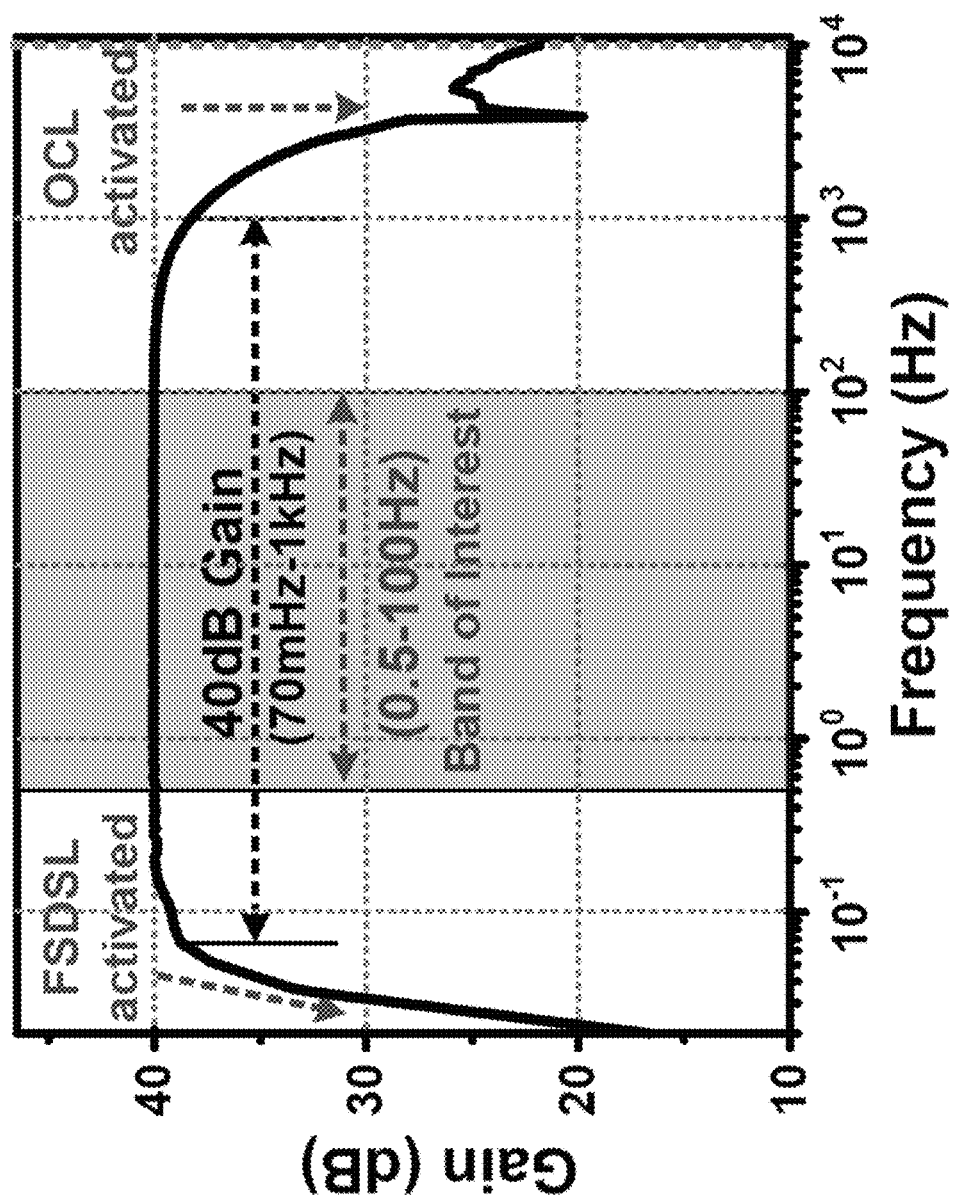
FIG. 20 generally illustrates measured gain-bandwidth curve of the DCCR CS-CCIA consistent with at least one embodiment of the present disclosure.

Turning now to FIGS. 19A and 19B, measurement results of a DCCR AFE 16 consistent with at least one embodiment of the present disclosure are generally illustrated. In particular, FIG. 19A generally illustrates the measured integrated noise Referred-To-Input (RTI) of the CS-CCIA (0.80 $\mu V_{rms}$ (0.5-100 Hz)). In contrast, FIG. 19B generally illustrates that the DCCR CS-CCIA 22 measures 0.90 $\mu V_{rms}$ (0.5-100 Hz) for single channel. A minimal noise elevation of 12% is observed by addition of the DC-CHOP 60 for channel sharing. With reference to FIG. 20, the GBW curve for the DCCR CS-CCIA 22 demonstrates a bandwidth of 70 mHz-1 kHz with gain of 40 dB, the OCL suppress the chopping frequency at 4 kHz and the modulated low frequency noise can be attenuated by more than −30 dB. Once the DSL 70 is activated, transfer curve will become an AC coupled with sub-100 mHz high pass corner; transfer curve shows similar performance to that of a CS-CCIA. The DCCR CS-CCIA 22 consumes 0.9 $\mu A$ at 1.8V power supply, resulting into 43.7% less power consumption compared to a CS-CCIA and with NEF of 3.29/channel, which is superior over that of other known systems. It should be noted that for the most of the time, CS-CCIA operates in seizure detection mode with pass-band up to 30 Hz, and the pass-band of 100 Hz is utilized only during recording mode. With reference to FIG. 21, a table is provided that summarizes the performance comparison of channel shared DCCR-AFE 16 with other known systems.

The performance of the D²A classification processor 18 has been validated using the Children's Hospital Boston (CHB)—MIT EEG database, which contains 906 hours of EEG data for 23 epileptic patients with 198 seizure events of various lengths in total. The number of seizure events per patient with corresponding patient age is plotted in FIG. 22. In particular, FIG. 22A provides an indication about the variance of patients verified by the implemented processors. Hold-out validation method has been used to evaluate the performance of D²A classification processor 18. FIG. 22B shows the total number of seizure and seizure patterns used for training per patient, the length of training datasets is 600 s for each patient. The training dataset per patient includes seizure pattern (ictal), preceded (pre-itcal) and followed (post-ictal) by normal EEG pattern. Weights for the WAA of corresponding channels are evaluated by using the same training sets. In one embodiment, the best training parameters for LSVM are introduced using Bioinformatics Toolbox. These parameters can play a significant influence on the classifier performance, trading-off between sensitivity and specificity. More specifically, increasing the penalty parameter "box-constraint" leads to a decrement in sensitivity and an increment in specificity; and vice versa. The range of chosen value was [10⁻⁴, 10], and 1 (default) was used for most of the patients.

These specific patient training parameters are evaluated off-chip and uploaded directly to the processor 18 for D²A-LSVM engine seizure classification using the external interface of the SoC 10. The sensitivity and specificity is defined by:

$$\text{Sensitivity} = \frac{\text{True Positive}}{\text{True Positive} + \text{False Negative}} \quad (9)$$

$$\text{Specificity} = \frac{\text{True Negative}}{\text{False Positive} + \text{True Negative}} \quad (10)$$

Figure 23:
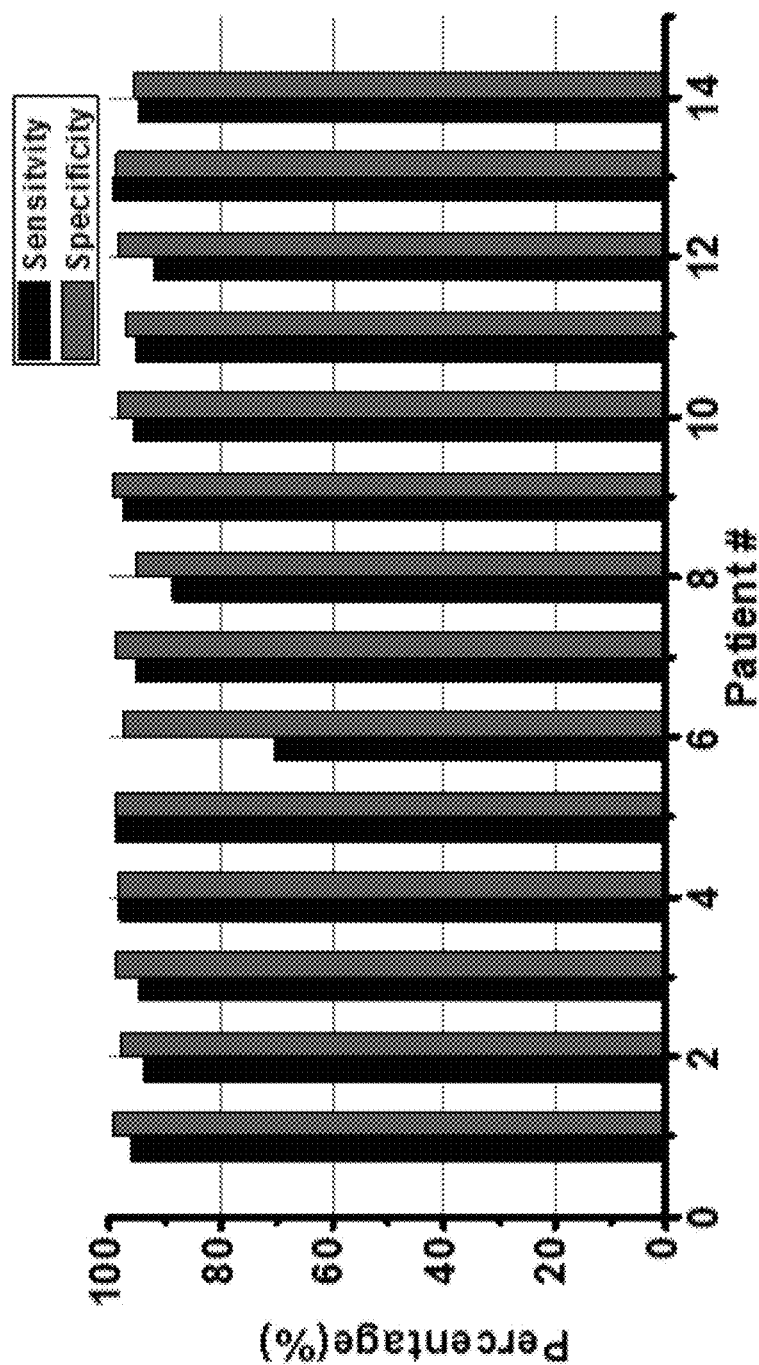
FIG. 23 generally illustrates $D^2A$ classification processor results with the CHB-MIT EEG datable consistent with at least one embodiment of the present disclosure with other systems.
Figure 24B:
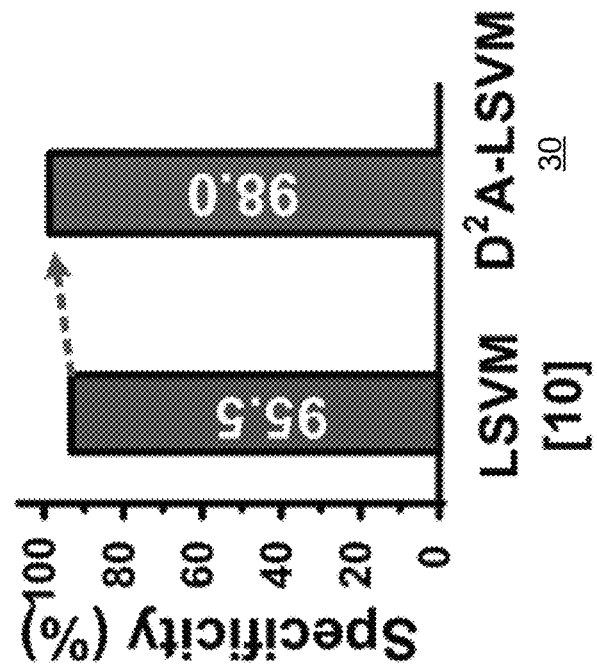
FIG. 24B generally illustrates a comparison of the specificity of LSVM compared with the $D^2A$-LSVM consistent with at least one embodiment of the present disclosure.
Figure 24A:
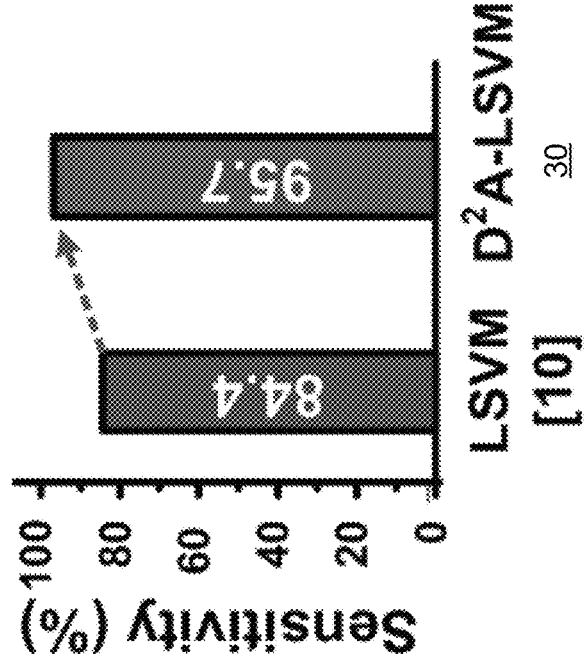
FIG. 24A generally illustrates a comparison of the sensitivity of LSVM compared with the $D^2A$-LSVM consistent with at least one embodiment of the present disclosure.

FIG. 23 generally illustrates the classification results (sensitivity and specificity) for the patients in CHB-MIT EEG database. This validation process reveals that the EEG processor 18 achieves an average sensitivity of 95.7% with an average specificity of 98% (0.27 false alarms/hour). FIG. 24 generally illustrates a comparison of the sensitivity, the specificity, and the latency of the D²A-LSVM 30 of the present disclosure with a known LSVM. The sensitivity and specificity of the D²A-LSVM 30 of the present disclosure is improved by 13.38% and 2.62%, respectively while the latency of the D²A-LSVM 30 of the present disclosure is reduced significantly by 50% in comparison to LSVM. With reference to FIG. 25, Table II compares the D²A classification processor 18 of the present disclosure with previous systems on EEG classification for epilepsy. The classifier 18 consumes 1.85 μJ/Classification for 16-channel operation with first time on-chip end of seizure detection with patient-specific approach.

Figure 26:
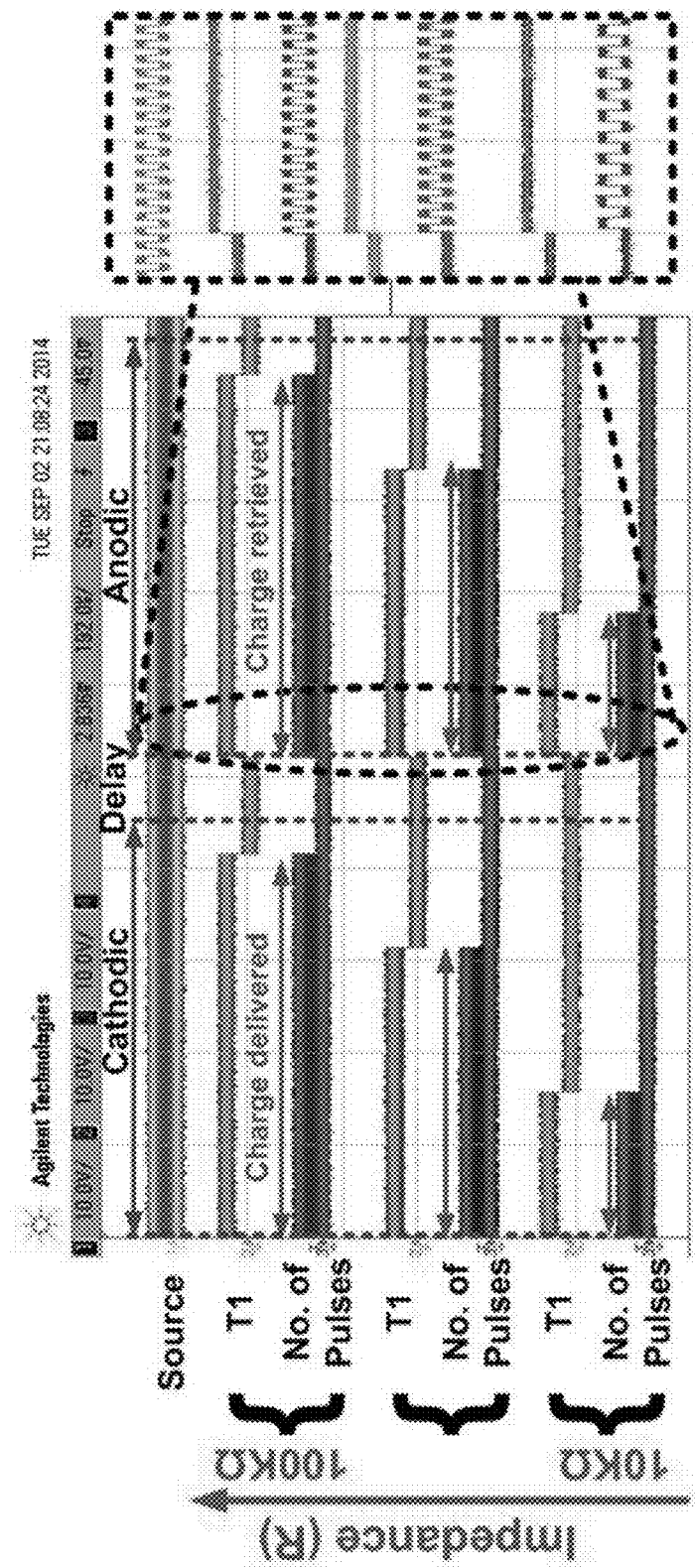
FIG. 26 generally illustrates measurement results of the PVTES with impedance variation adaptability consistent with at least one embodiment of the present disclosure.

FIG. 26 generally illustrates the measurement result of the PVTES 20, showing constant charge delivery for different resistance variation by adapting the number of stimulation pulses correspondingly. It confirms the impedance adaptive variation from 10 kΩ to 100 kΩ, which is resistance variation reported during tES. Also, it verifies the charge delivered in cathodic phase is retrieved back in anodic phase for all different resistance scenarios. The implemented PVTES 20 successfully adapts to impedance variation of different patients while consuming only 2.45 μW, which is 59% less power consumption as compared to other treatment systems.

Figure 27:
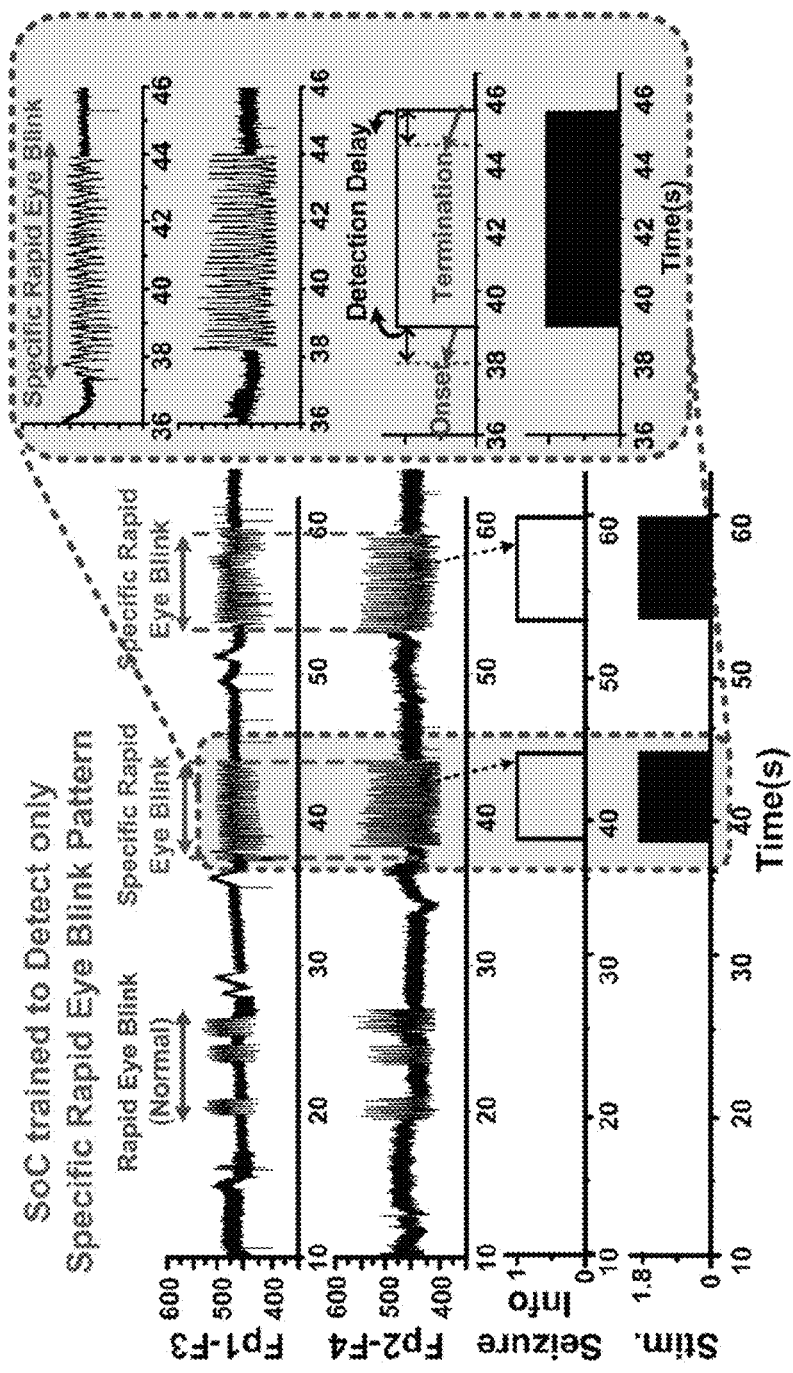
FIG. 27 generally illustrates SoC measurement with specific rapid-eye blink classification consistent with at least one embodiment of the present disclosure.

FIG. 27 shows the overall SoC 10 verification results with a rapid-eye blink detection test for 4-channel mode. Some seizures accompany rapid eye blinking or repetitive eye movements. To test the full functionality of the SoC 10, it is trained for a specific rapid-eye blinking pattern as a scenario, and the continuous detection tests are performed. The electrodes are attached (Fp1-F3, Fp2-F4) to verify that during 2 hours of continuous operation, the SoC 10 is able to detect the trained specific eye blink patterns with sensitivity and specificity of 92% and 97%, respectively. The measured classification results are far better other known systems (e.g., LSVM alone) and comparable to NLSVM, but with significantly reduced uploading parameters and interface wires. The measurement also verifies the simultaneous triggering of PVTES pulses along with the specific eye-blink pattern start-and-end detection.

Figure 28:
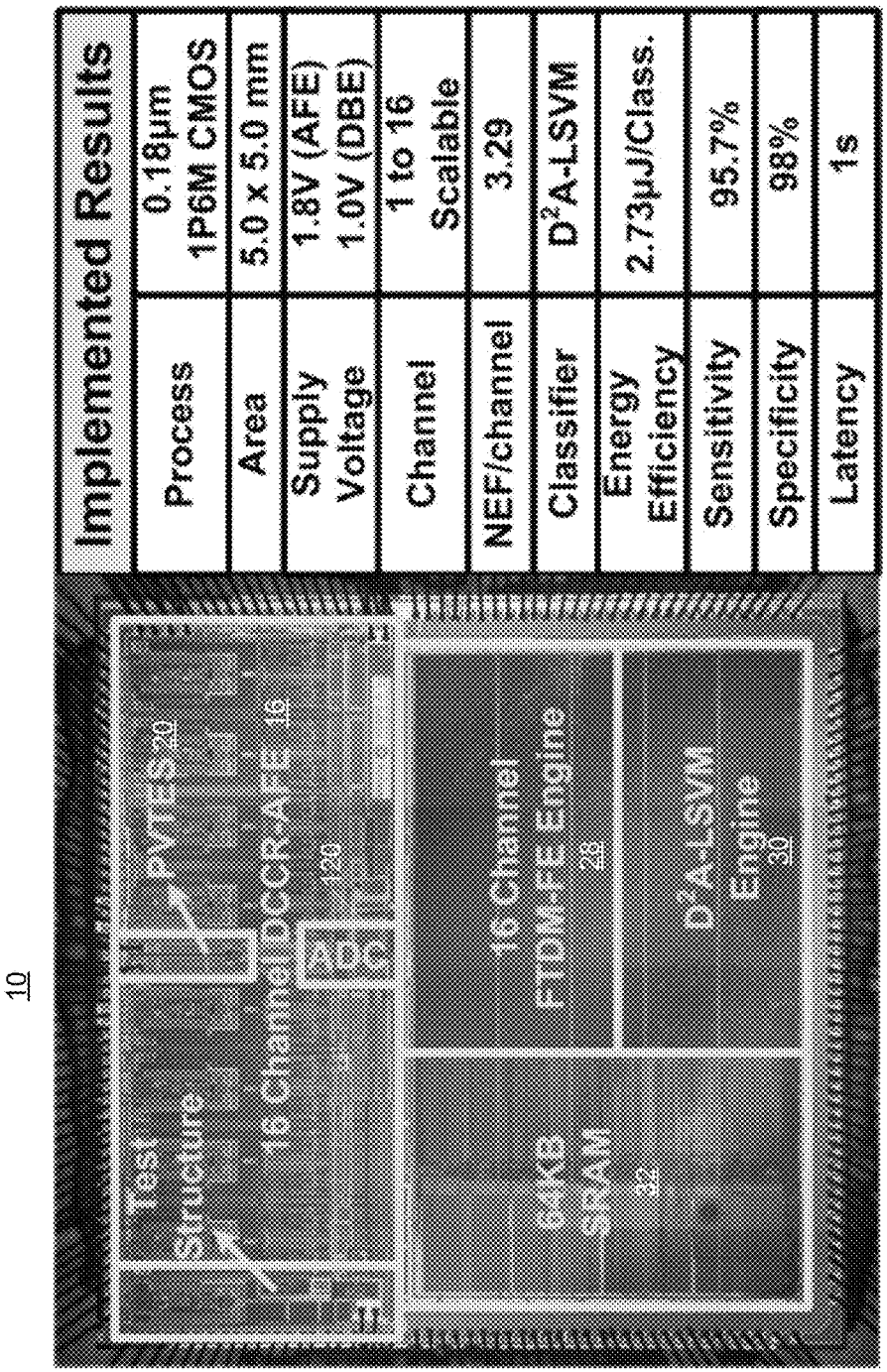
FIG. 28 generally illustrates SoC micrograph and performance summary consistent with at least one embodiment of the present disclosure.

FIG. 28 shows one embodiment of the SoC 10 micrograph and its performance summary. The 25 mm² 0.18 μm 1P6M CMOS chip 10 fully integrates a 16-channel DCCR-AFE 16, D²A-LSVM engine 30, 16-channel FE engine 28, A/D 120, 64 kB SRAM 32 and PVTES 20, at 2.73 μJ/Classification to continuously track seizure onset and termination with precise stimulation to suppress the patient-specific seizure activity.

Figure 29:
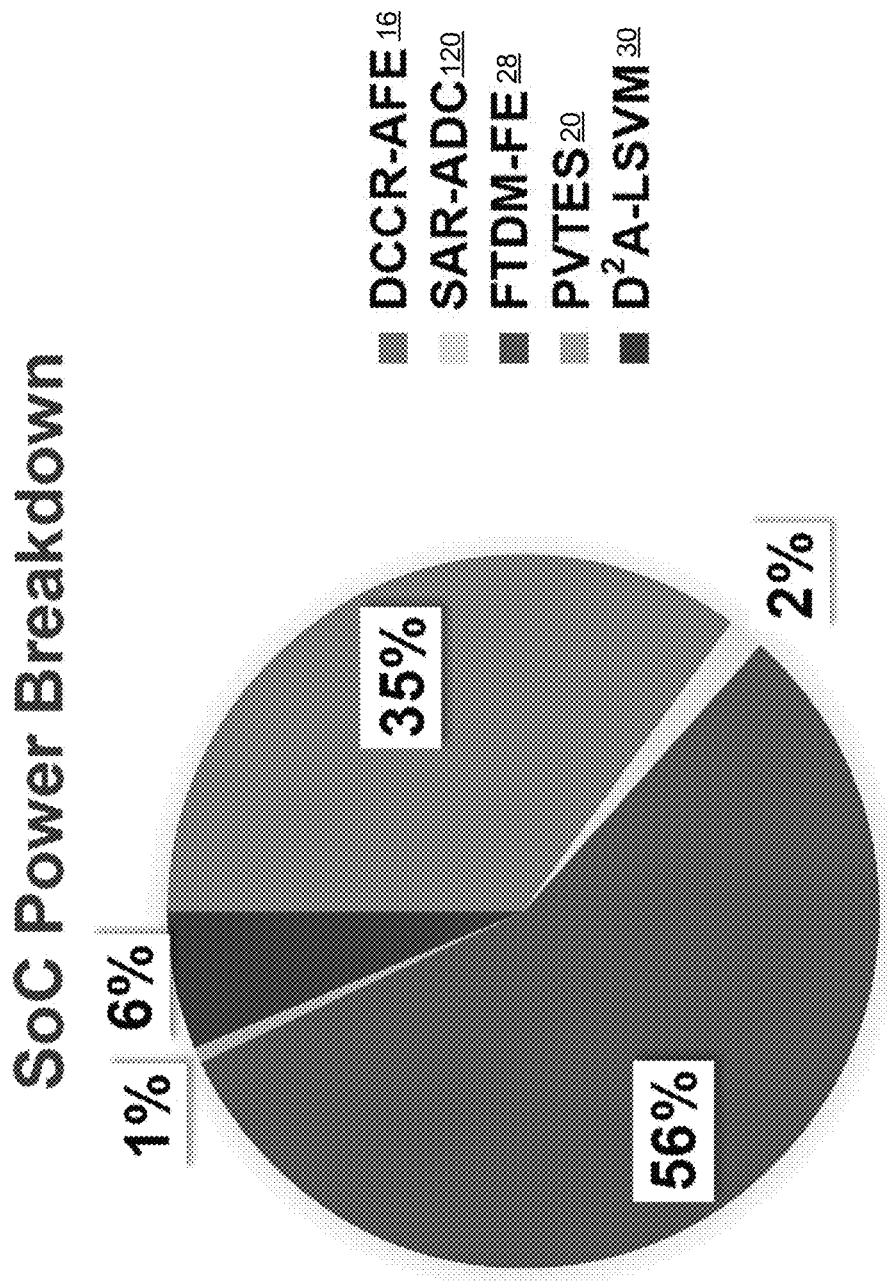
FIG. 29 generally illustrates overall SoC power breakdown consistent with at least one embodiment of the present disclosure.

FIG. 29 graphically illustrates one embodiment of the power breakdown of the SoC 10 for 16-channel operation. The SoC 10 features scalable channels (e.g., up to 16) with the fully integrated readout circuits, the patient specific $D^2A$ classification processor 18 seizure onset and termination detection classifier with on-chip non-invasive stimulator 20. The AFE 16 consumes 0.9 μA/channel with a noise RTI is 0.90 $\mu V_{rms}$ with an energy consumption of 2.73 μJ/classification.

Turning back to FIG. 2, the SoC 10 of the present disclosure may includes, inter alia, a 16-channel AFE system 16 that may include eight dual-channel charge recycled (DCCR) Chopper-Stabilized Capacitive-Coupled IA (CS-CCIA) 22, that may operate in continuous time domain (e.g., 40 dB/1 kHz). Each channel (e.g., CH1, CH2) may be followed by a discrete time-domain PGA 26a, 26b (programmable gain, e.g., 12/20/32/40 dB and bandwidth 100/30 Hz). To provide accurate stimulation, the machine learning DBE 18 performs patient-specific seizure onset and termination detection with a 16-channel feature extraction engine (FE) 28 using frequency and time division multiplex BPF (FTDM-BFP) 29, a linear-SVM (LSVM) classifier-based on dual detector architecture ($D^2A$) engine 30, an on-chip memory 32 (e.g., 64 KB SRAM for EEG data storage, and (optionally) a non-invasive closed-loop PVTES 20. Improvements of these embodiments would include a higher performing processor and EEG data storage capacity. Other improvements include new electrode designs and configurations.

Turning back to FIG. 3, to minimize surface area and power consumption, every two channels CH1, CH2 share a CS-CCIA 22 by a chopper-MUX (CPMUX) 60 and fast settling DC Servo Loop (FS-DSL) 70. The DCCR CS-CCIA recycles the bias current between the two channels (CH1, CH2) to decrease the effective current consumption, e.g., by nearly half (e.g., 0.90 μA/ch and NEF 3.29/ch), but in contrast elevated the noise by only 10% (e.g., 0.90 $\mu V_{rms}$ 0.5-100 Hz). The integration of SoC 10 on patch type sensors lead to increased electrode DC offset (EDO) that may result in the FS-DSL 70 with a sharp high-pass filter characteristic to reject the EDO.

To overcome the settling time startup that can reach up to several hours for EDO of approximately 240 mV, the SoC 10 (e.g., patch sensor) may include a FS-DSL to control the pseudo-resistor (PMOS) resistance with nRST at startup to facilitate quick set-up. Settling time of 1 s may be achieved by adding an extra GM though this consumes 58 μA/ch. In contrast, the FS-DSL 70 settles within 0.5 s without any area or power penalty. To ensure switching between the two channels (CH1, CH2) that have different EDOs, and to overcome the slew rate while switching, the last known intermediate node values for each channel (CH1, CH2) are sampled to $C_{DSL-CH1}$ 40, $C_{DSL-CH2}$ 42. Specifically, the first channel (CH1) is in amplification phase, when the second channel (CH2) is being sampled and vice versa. Measurement results consistent with at least one embodiment of the AFE 16 (FIGS. 19A and 19B) demonstrate the operation of the DCCR 22 with 180 degree out-of-phase inputs for each channel (CH1, CH2), which is the worst case scenario. The switching frequency between channels (CH1, CH2) was selected as 1 KHz that correlated double sampling (CDS) based PGA sampling at 8 kHz, which mitigated the residual offset caused by the charge injection due to channel switching in addition to the chopper switch 60.

Turning back to FIG. 9, one embodiment of the classification processor 18 (e.g., a 16-channel DBE) is generally illustrated. In this embodiment, a Weight and Average algorithm 80 is used with a $D^2A$ classification engine 30 for more precise seizure onset/termination detection. The $D^2A$ classification with patient specific threshold value may be implemented for false alarm suppressing and accuracy boosting. In $D^2A$ application, two LSVM detectors 94a, 94b targeting on sensitivity and specificity are operating in parallel and the preliminary classification results are fed into the arbiter 96 for final decision, which controls on-chip 10 data storage and PVTES. Moreover, condensed training allowed expanded training set from 160 s to approximately 2500 s with more non-seizure patterns. This embodiment surprisingly improved the sensitivity and specificity to 92.5% and 97%, respectively, in the presence of LSVM. In addition, the FE engine 28 uses the 2 s sliding window overlapped by 1 s to reduce the latency to 1 s. This resulted in latency by 50% reduction permitting faster response to seizures. Other improvements included reduced memory requirements for Support Vectors.

With reference back to FIG. 10, a 16-ch SoC 10 with $D^2A$ 18 may be incorporated within the same die size as an 8-ch single detector SoC using a FTDM-BPF 28, 29. Input data for 16 channels are stored in parallel in 16×46-tap FIFOs 82 (e.g., at 128 Hz). BPF coefficients for 7 banks 83 are multiplexed (e.g., using MUX 87) into coefficient cache 84 (e.g., at 1 KHz). With one clock cycle (e.g., of 1 KHz), 16 channels of data in FIFOs 821 are multiplex (e.g., using MUX 86) into the data cache 8 of a single BPF 90 (e.g., at 16 KHz) to calculate outputs of one specific bank for all 16 channels. Subsequently, it is de-multiplexed (e.g., using DEMUX 92) to corresponding banks 93 in corresponding channels. In the unique design, FTDM-BPF 28, 29 only uses 16×46-tap FIFOs 82, seven BPF coefficient register groups 83, and a single 46-tap BPF 90 (e.g., at 16 KHz) to process FE for 16 channels. This design shrunk the date number of FE engine by 57.6% and 40.5% compared with 16-channel DQ-LUT and 16-channel TDM-BPF, respectively, while consuming only 1.85 58 μJ/Classification overall.

With reference back to FIG. 16, one embodiment of the patient specific treatment circuitry 20 is generally illustrated implemented as a PVTES having real time impedance monitoring, without the need for constant current injection, to timely suppress the clinical onset beforehand. A major drawback of known voltage mode stimulation systems is the skin impedance variation between and within a patient that makes it very difficult to ensure constant charge delivery. It also consumes 32 μA-2 mA based on the current mirror circuit, but fails to take into account impedance variation and charge balancing. The use of an additional pseudo sinusoidal current source to monitor the impedance with high resolution at the cost of extra power consumption (18 μW). In this embodiment, the PVTES 20 exploits the RC relaxation variation due to the skin impedance variation (approximately 5 KΩ-200 KΩ) that resulted in different counter values. A further parameter is that the PVTES 20 adapts the number of 1 MHz biphasic stimulation pulses with charge balancing to ensure constant charge delivery. This embodiment provided impedance variation with significantly lower power (<2.6 μW) and area utilization.

According to one aspect, the present disclosure features a system on chip (SoC) with reduction power consumption and area. The SoC includes comprising an analog front-end (AFE) configured to receive a plurality of differential input channels and generate digitized data corresponding to the plurality of differential input channels, and a classification processor configured to receive the digitized data from the AFE. The AFE includes a Dual-Channel Chopper (DC-CHOP) configured to perform channel multiplexing of a first and a second differential input channel of the plurality of differential input channels while simultaneously chopping the first and the second differential input channel, a Dual Channel Charge Recycled-AFE (DCCR-AFE) having an Chopper-Stabilized Capacitive-Coupled IA (CS-CCIA) including bias sampling capacitors that store bias values associated with the first and the second differential input channel to enable swapping between the channel, and a DC servo loop, wherein a setting time of the DC servo loop is reduced based on a reduction in a resistance of the pseudo-resistor (PMOS) of the DC servo loop in response to engaging a system reset (nRST). The classification processor includes a Frequency-Time Division Multiplexing (FTDM) Feature Extraction (FE) engine and a Dual-Detector Architecture ($D^2A$) classification processor. The FTDM-FE includes a plurality of FIFOs configured to store, in parallel, the digitized data corresponding to the plurality of differential input channels, a plurality of band-pass filter (BPF) banks storing BPF coefficients, and a single BPF to calculate outputs of one specific bank of the plurality of BFP banks for all of the plurality of differential input channels. The $D^2A$ classification processor is configured to receive the output data from the FTDM-FE and to approximate a beginning and an end of a seizure. The $D^2A$ classification processor includes a first Linear Support-Vector Machine (LSVM) optimized for only sensitivity and a second LSVM optimized only specificity.

Optionally, the SoC may include skin-electrode impedance variation adaptation circuitry including stimulation signal circuitry to generate electrical stimulating pulses to be applied to a patient's skin through one or more electrodes. The stimulation signal circuitry is configured to generate the electrical stimulating pulses based on the electrical stimulating pulses such that the stimulation signal circuitry automatically adapts a number of pulses with respect to skin-electrode impedance variation to ensure constant charge delivery.

According to another aspect, the present disclosure features a analog front-end (AFE). The AFE is configured to receive a plurality of differential input channels and includes a DC servo loop (DSL). A fast setting time of the DSL is reduced based on temporarily reduction in a resistance of the pseudo-resistor (PMOS) of the DSL in response to engaging a system reset (nRST) followed by disengaging nRST. The AFE may be part of a SoC, however, it should be appreciated that the AFE may be used in any multi-channel AFE to save power and reduce area.

According to a further aspect, the present disclosure features an analog front-end (AFE). The AFE is configured to receive a plurality of differential input channels and includes a DC servo loop (DSL). A fast setting time of the DSL is reduced based on temporarily reduction in a resistance of the pseudo-resistor (PMOS) of the DSL in response to engaging a system reset (nRST) followed by disengaging nRST. The AFE may be part of a SoC, however, it should be appreciated that the AFE may be used in any multi-channel AFE to save power and reduce area.

According to yet another aspect, the present disclosure features skin-electrode impedance variation adaptation circuitry. The skin-electrode impedance variation adaptation circuitry includes stimulation signal circuitry to generate electrical stimulating pulses to be applied to a patient's skin through one or more electrodes. The stimulation signal circuitry is configured to generate the electrical stimulating pulses based on the electrical stimulating pulses such that the stimulation signal circuitry automatically adapts a number of pulses with respect to skin-electrode impedance variation to ensure constant charge delivery.

According to an additional aspect, the present disclosure features an AFE with charge recycling. The CS-CCIA adopts bias sampling capacitors that store the bias value (e.g., acts as a bias memory) to enable quick settling upon swapping the channel. A Dual-Channel Chopper (DC-CHOP) is configured to perform channel MUXing function at the same time as chopping, without any additional hardware. The AFE may be part of a SoC, however, the AFE may be used in any multi-channel AFE to save power and area, and is therefore not limited to a SoC unless specifically claimed as such.

According to another aspect, the present disclosure features an AFE including a DC servo loop (DSL) with fast setting time. System reset (e.g., nRST) is combining with FS-DSL to enable fast settling of DSL. DSL, which typically requires long initial settling time, is not only problematic in channel sharing amp, but biomedical readout circuit in general has the same issue of long settling time DSL.

According to a further aspect, the present disclosure features skin-electrode impedance variation adaptation circuitry. The skin-electrode impedance variation adaptation (such as, but not limited to, tES) can be used in any type of skin-electrode impedance monitoring purposes for applications that involve "pulses applied to skin through electrode." Known systems utilize both 1) a dedicated current injecting circuitry for impedance monitoring and 2) stimulation signal circuitry. The skin-electrode impedance variation adaptation circuitry of the present disclosure, in contrast, does not require a dedicated current injecting circuitry for impedance monitoring, and instead utilizes only use the stimulation pulse; the naturally occurring RC time constant from the stimulating pulse is monitored to extract the skin-electrode impedance information.

According to yet a further aspect, the present disclosure features a Frequency-Time Multiplexing Frequency Extraction Engine. The Frequency-Time Multiplexing Frequency Extraction Engine includes an analog front-end (AFE) and a classification processor. The AFE is configured to receive a plurality of differential input channels and generate digitized data corresponding to the plurality of differential input channels. The classification processor is configured to receive the digitized data from the AFE. The classification process includes a Frequency-Time Division Multiplexing (FTDM) Feature Extraction (FE) engine. The FTDM-FE includes a plurality of FIFOs configured to store, in parallel, the digitized data corresponding to the plurality of differential input channels, a plurality of band-pass filter (BPF) banks storing BPF coefficients, wherein each BPF processed in a separate frequency, and a single BPF to calculate outputs of one specific bank of the plurality of BFP banks for all of the plurality of differential input channels.

According to yet another aspect, the present disclosure features a L-SVM with digital hysteresis including an analog front-end (AFE) and a Dual-Detector Architecture ($D^2A$) classification processor. The AFE is configured to receive a plurality of differential input channels and generate digitized data corresponding to the plurality of differential input channels. The $D^2A$ classification processor is configured to receive the digitized data from the AFE and to approximate a beginning and an end of a seizure. The $D^2A$ classification processor includes a first classifier optimized for only sensitivity and a second classifier optimized only specificity, wherein outputs of the first and the second classifiers are summed and a digital hysteresis is applied to reduce false positives. Optionally, the first and the second classifiers include a first Linear Support-Vector Machine (LSVM) and a second LSVM, respectively. It should be appreciated that many different types of classifiers can be used instead of L-SVM such as, but not limited to, NL-SVM, neural network, decision tree, etc. Optionally, the digital hysteresis includes a Patient Specific Threshold (PST), and wherein the PST is established by supervised learning or using a self-learning algorithm.

According to another aspect, the present disclosure features a Frequency-Time Division Multiplexing (FTDM) Feature Extraction (FE). The FTDM-FE may include, but is not limited to, 16 channels. For example, the FTDM-FE may therefore include greater than, or less than, 16 channels.

According to yet a further aspect, the present disclosure features a Dual detector Architecture processor. With known systems and methods, it is very difficult to achieve sensitivity and specificity at the same time (improving one decreases the other). The Dual detector architecture processor of the present disclosure may include two L-SVM with each optimized to sensitivity and specificity only. As described herein, the L-SVM of the present disclosure performs achieves performance similar to that of a NL-SVM. The Dual detector Architecture processor of the present disclosure is configured to not only detect the beginning of a seizure, but is also configured to detect the end of seizure. The Dual detector Architecture processor of the present disclosure also includes digital hysteresis to reduce and/or eliminate false alarms.

The foregoing description of example embodiments has been presented for the purposes of illustration and description. It is not intended to be exhaustive or to limit the present disclosure to the precise forms disclosed. Many modifications and variations are possible in light of this disclosure. It is intended that the scope of the present disclosure be limited not by this detailed description, but rather by the claims appended hereto. Future filed applications claiming priority to this application may claim the disclosed subject matter in a different manner, and may generally include any set of one or more limitations as variously disclosed or otherwise demonstrated herein.

What is claimed is:

1. A system on chip (SoC) with reduction power consumption and area comprising:
   an analog front-end (AFE) configured to receive a plurality of differential input channels and generate digitized data corresponding to said plurality of differential input channels, said AFE comprising:
      a Dual-Channel Chopper (DC-CHOP) configured to perform channel multiplexing of a first and a second differential input channel of said plurality of differential input channels while simultaneously chopping said first and said second differential input channel;
      a Dual Channel Charge Recycled-AFE (DCCR-AFE) having a Chopper-Stabilized Capacitive-Coupled Instrumentation Amplifier (CS-CCIA) including bias sampling capacitors that store bias values associated with said first and said second differential input channel to enable switching between said first and said second differential input channel; and
      a DC servo loop, wherein a setting time of said DC servo loop is reduced based on a reduction in a resistance of a pseudo-resistor (PMOS) of said DC servo loop in response to engaging a system reset (nRST) followed by disengaging nRST; and
   a classification processor configured to receive said digitized data from said AFE, said classification processor comprising:
      a Frequency-Time Division Multiplexing (FTDM) Feature Extraction (FE) engine comprising:
         a plurality of first-in-first-outs (FIFOs) configured to store, in parallel, said digitized data corresponding to said plurality of differential input channels;
         a plurality of band-pass filter (BPF) banks storing BPF coefficients, wherein each BPF allows signals to pass within a particular, separate frequency band; and
         a single BPF to calculate outputs of one specific bank of said plurality of BPF banks for all of said plurality of differential input channels; and
      a Dual-Detector Architecture ($D^2A$) classification processor configured to receive said output data from said FTDM-FE and to approximate a beginning and an end of a seizure, said $D^2A$ classification processor comprising a first classifier optimized for only sensitivity and a second classifier optimized for only specificity.

2. The SoC of claim 1, further comprising:
skin-electrode impedance variation adaptation circuitry comprising stimulation signal circuitry to generate electrical stimulating pulses to be applied to a patient's skin through one or more electrodes, said stimulation signal circuitry configured to generate said electrical stimulating pulses such that said stimulation signal circuitry automatically adapts a number of pulses with respect to skin-electrode impedance variation to ensure constant charge delivery.

3. The SoC of claim 1,
wherein outputs of said first and said second classifiers are summed and a digital hysteresis is applied to reduce false positives.

4. The SoC of claim 3, wherein said first and said second classifiers include a first Linear Support-Vector Machine (LSVM) and a second LSVM, respectively.

5. The SoC of claim 3, wherein said digital hysteresis includes a Patient Specific Threshold (PST), and wherein said PST is established by supervised learning or using a self-learning algorithm.

6. A channel sharing analog front-end (AFE) configured to receive a plurality of differential input channels, said AFE comprising:
   a Dual-Channel Chopper (DC-CHOP) configured to perform channel multiplexing of a first and a second differential input channel of said plurality of differential input channels while simultaneously chopping said first and said second differential input channel; and
   a Dual Channel Charge Recycled-AFE (DCCR-AFE) having a Chopper-Stabilized Capacitive-Coupled Instrumentation Amplifier (CS-CCIA) including a plurality of output channels, and bias sampling capacitors that store bias values associated with said first and said second differential input channel to enable swapping between said first and said second differential input channel.

7. The AFE of claim 6, further comprising a first and a second programmable gain amplifier (PGA) configured to amplify each of said output channels of said CS-CCIA.

8. The AFE of claim 6, further comprising a DC servo loop, wherein a setting time of said DC servo loop is reduced based on a temporary reduction in a resistance of a pseudo-resistor (PMOS) of said DC servo loop in response to engaging a system reset (nRST).

9. An analog front-end (AFE) configured to receive a plurality of differential input channels, said AFE comprising:
a DC servo loop (DSL), wherein a fast setting time of said DSL is reduced based on a temporary reduction in a resistance of a pseudo-resistor (PMOS) of said DSL in response to engaging a system reset (nRST) followed by disengaging nRST.

10. The AFE of claim 9, wherein said DSL's pseudo-resistor (PMOS) gate is connected to a ground (GND) when said nRST is engaged.

11. The AFE of claim 9, wherein said DSL's pseudo-resistor (PMOS) gate is coupled to supply voltage VDD when said nRST is disengaged.

12. The AFE of claim 9, wherein said DSL has a settling time of 0.5 second or less.

13. A Frequency-Time Multiplexing Frequency Extraction Engine comprising:
an analog front-end (AFE) configured to receive a plurality of differential input channels and generate digitized data corresponding to said plurality of differential input channels; and
a classification processor configured to receive said digitized data from said AFE, said classification processor comprising a Frequency-Time Division Multiplexing (FTDM) Feature Extraction (FE) engine comprising:
a plurality of FIFOs configured to store, in parallel, said digitized data corresponding to said plurality of differential input channels;
a plurality of band-pass filter (BPF) banks storing BPF coefficients, wherein each BPF allows signals to pass within a particular, separate frequency band; and
a single BPF to calculate outputs of one specific bank of said plurality of BPF banks for all of said plurality of differential input channels.

14. The Frequency-Time Multiplexing Frequency Extraction Engine of claim 13, wherein said single BPF comprises:
a data cache for storing digitized data multiplexed from said plurality of FIFOs; and
at least one coefficients cache for storing said BPF coefficients from said plurality of BPF banks.

15. The Frequency-Time Multiplexing Frequency Extraction Engine of claim 14, where said plurality of differential input channels is equal to N channels, and wherein digitized input data corresponding to said N channels are stored in parallel in N number of multi-tap FIFOs of said FTDM-FE.

16. The Frequency-Time Multiplexing Frequency Extraction Engine of claim 13, wherein said FTDM-FE implements 2 s overlapped window with 1 s increment epoch windowing design.

* * * * *